(12) United States Patent
Castel et al.

(10) Patent No.: US 7,660,636 B2
(45) Date of Patent: Feb. 9, 2010

(54) ELECTRICAL STIMULATION DEVICE AND METHOD FOR THE TREATMENT OF DYSPHAGIA

(75) Inventors: J. Chris Castel, Washoe, NV (US); Francis X. Palermo, Washoe, NV (US)

(73) Assignee: Accelerated Care Plus Corp., Reno, NV (US)

( * ) Notice: Subject to any disclaimer, the term of this patent is extended or adjusted under 35 U.S.C. 154(b) by 386 days.

(21) Appl. No.: 11/325,196

(22) Filed: Jan. 4, 2006

(65) Prior Publication Data

US 2007/0156182 A1 Jul. 5, 2007

(51) Int. Cl.
*A61N 1/18* (2006.01)
(52) U.S. Cl. .............................. 607/148; 607/2; 607/42; 607/118
(58) Field of Classification Search ...................... 607/2, 607/42, 46, 134, 907; 128/898
See application file for complete search history.

(56) References Cited

U.S. PATENT DOCUMENTS

| | | | |
|---|---|---|---|
| 3,902,502 | A | 9/1975 | Liss et al. |
| 4,023,574 | A | 5/1977 | Nemec |
| 4,444,205 | A | 4/1984 | Jackson |
| 5,109,847 | A | 5/1992 | Liss et al. |
| 5,190,053 | A | 3/1993 | Meer |
| 5,562,718 | A | 10/1996 | Palermo |
| 5,725,564 | A | 3/1998 | Freed et al. |
| 5,834,051 | A | 11/1998 | Woloszko et al. |
| 5,851,223 | A | 12/1998 | Liss et al. |
| 5,891,185 | A | 4/1999 | Freed et al. |

(Continued)

FOREIGN PATENT DOCUMENTS

WO WO 95/33516 12/1995

(Continued)

OTHER PUBLICATIONS

Boswell, NS, *Net Neuroelectric Therapy Eliminates Xerostomia During Radiotherapy-A Case Study*, Am. Journal of Electromedicine, Feb. 1989, 105-107.

(Continued)

*Primary Examiner*—Carl H Layno
*Assistant Examiner*—Natasha N Patel
(74) *Attorney, Agent, or Firm*—Stinson Morrison Hecker LLP

(57) ABSTRACT

An electrical stimulation device and method for the treatment of dysphagia is disclosed. In a preferred embodiment, the electrical stimulation device includes one or more channels of electrodes each of which includes a first electrode positioned in electrical contact with tissue of a target region of a patient and a second electrode positioned in electrical contact with tissue of a posterior neck region or a posterior thoracic region of the patient. A series of electrical pulses are then applied to the patient through the one or more channels of electrodes in accordance with a procedure for treating dysphagia. The series of electrical pulses may comprise: a plurality of cycles of a biphasic sequential pulse train pattern; a plurality of cycles of a biphasic overlapping pulse train pattern; a plurality of cycles of a triphasic sequential pulse train pattern; a plurality of cycles of a triphasic overlapping pulse train pattern; a functional pulse train pattern; a low-frequency pulse train pattern; or a frequency-sequenced pulse burst train pattern. Various exemplary embodiments of the invention are disclosed.

51 Claims, 9 Drawing Sheets

U.S. PATENT DOCUMENTS

| | | | |
|---|---|---|---|
| 5,987,359 | A | 11/1999 | Freed et al. |
| 6,058,938 | A | 5/2000 | Chu et al. |
| 6,104,958 | A | 8/2000 | Freed et al. |
| 6,198,970 | B1 | 3/2001 | Freed et al. |
| 6,484,053 | B2 | 11/2002 | Leelamanit et al. |
| 6,572,594 | B2 | 6/2003 | Satterfield et al. |
| 7,010,345 | B2 * | 3/2006 | Hill et al. ............. 607/10 |
| 7,039,468 | B2 | 5/2006 | Freed et al. |
| 2002/0010495 | A1 | 1/2002 | Freed et al. |
| 2002/0161416 | A1 | 10/2002 | Huang |
| 2003/0093128 | A1 | 5/2003 | Freed et al. |
| 2004/0220645 | A1 * | 11/2004 | Freed et al. ............. 607/48 |

FOREIGN PATENT DOCUMENTS

| | | |
|---|---|---|
| WO | WO 2004/028433 | 4/2004 |

OTHER PUBLICATIONS

Boswell, et al., *Noninvasive Electrical Stimulation for the Treatment of Radiotherapy Side-Effects*, Am. Journal of Electromedicine, 2(3), 1985.

Kaada, B. *Successful Treatment of Esophageal Dysmotility and Raynaud's Phenomenon in Systemic Sclerosis and Achalasia by Transcutaneous Nerve Stimulation. Increase in Plasma VIP Concentration*, Canadian Journal of Gastroenterology, 1137-1146, vol. 22, No. 9, 1987,Norwegian University Press.

Broniatowski, et al., *New horizons in dynamic rehabilitation of paralyzed laryngeal functions*, Department of Otolaryngology, Cleveland Clinic Foundation. Jul.-Sep. 1988; 34(3):674-80 (PubMed—PMID: 3196583).

Sanders, et al., *Transmucosal electrical stimulation of laryngeal muscles*, Sloths Research Laboratory, Department of Otolaryngology, Mount Sinai Medical Center, New York, NY, 10029, May 1989; 98(5 Pt 1): 339-45 (PubMed—PMID: 2719451).

Guelrud, et al., *Transcutaneous Electrical Nerve Stimulation Decreases Lower Esophageal Sphincter Pressure in Patients with Achalasia*, Digestive Diseases and Sciences, Aug. 1991, 1029-1033, vol. 36, No. 8.

Talal, et al., *The clinical effects of electrostimulation on salivary function of Sjögren's syndrome patients. A placebo controlled study*, Rheumatology International, Jun. 1992, 43-45, vol. 12, No. 2.

Park, et al., *A pilot exploratory study of oral electrical stimulation on swallow function following stroke: an innovative technique*, South Manchester University Hospitals NHS Trust, Manchester, United Kingdom, 1997 Summer; 12(3):161-6. (PubMed—PMID: 9190102).

Cook, et al., *AGA Technical Review on Management of Oropharyngeal Dysphagia*, Gastroenterology Feb. 1999, 455-478, vol. 116, No. 2.

U.S. Appl. No. 11/711,285 (Inventors: Francis X. Palermo, J. Chris Castel) (Filing Date: Feb. 27, 2007).

Freed et al. "Electrical stimulation for swallowing disorders caused by stroke", RC Respiratory Care, Daedalus Enterprises, Inc., United States, vol. 46, No. 5, May 1, 2001, pp. 466-474.

European Search Report date Oct. 19, 2009 for European Patent Application No. 07716324.4; 10 pages.

* cited by examiner

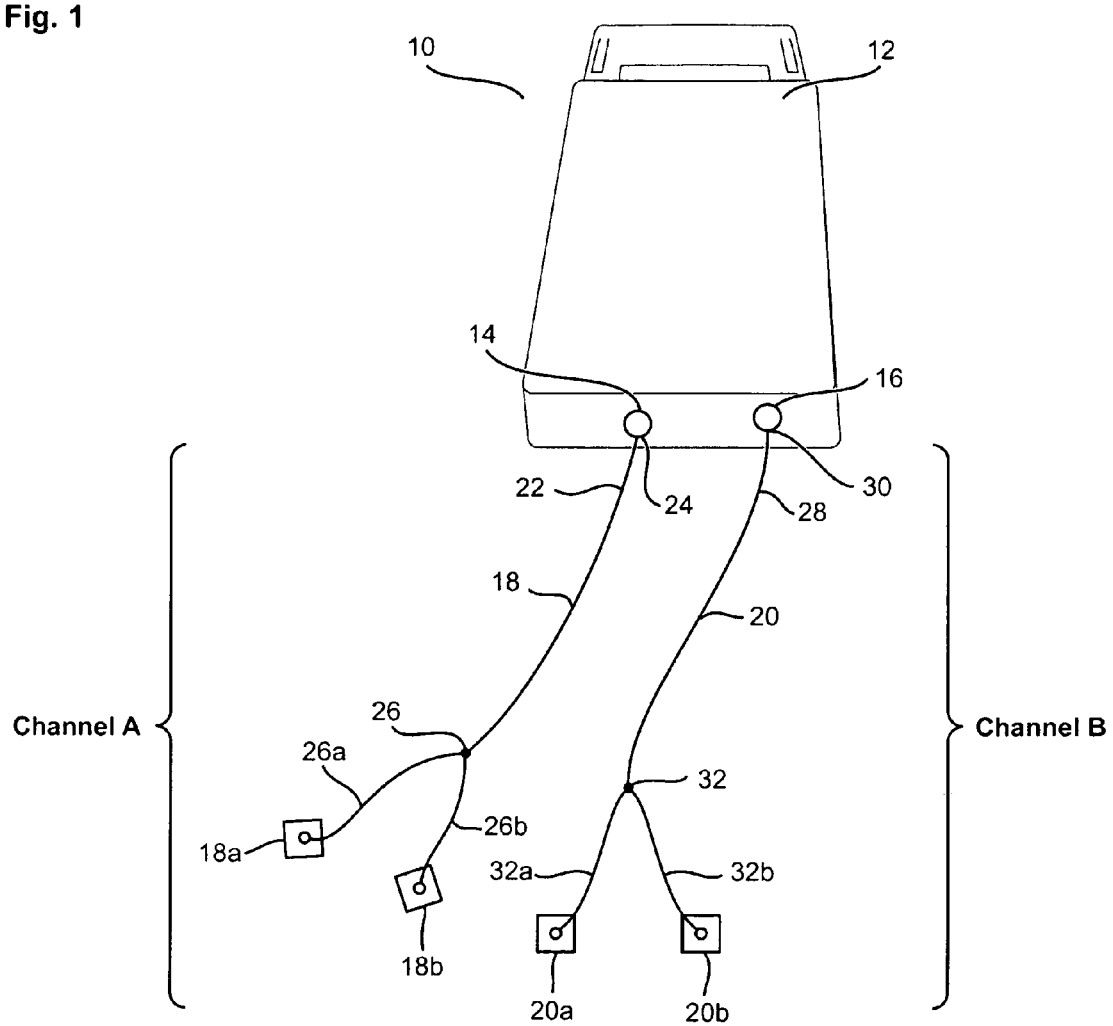

Channel A
Channel B

Channels fire simultaneously

Channel A
Channel B 1-5 Hz bursts
10-120 sec 5-20 Hz bursts
10-120 sec 20-250 Hz bursts
10-120 sec Channel A
Channel B 5-20 Hz bursts
2-10 minutes 1-5 Hz bursts
10-30 minutes 20-250 Hz bursts
10-20 minutes Channel A
Channel B 20-250 Hz bursts
10-20 minutes 1-20 Hz bursts
10-20 minutes Fig. 3C
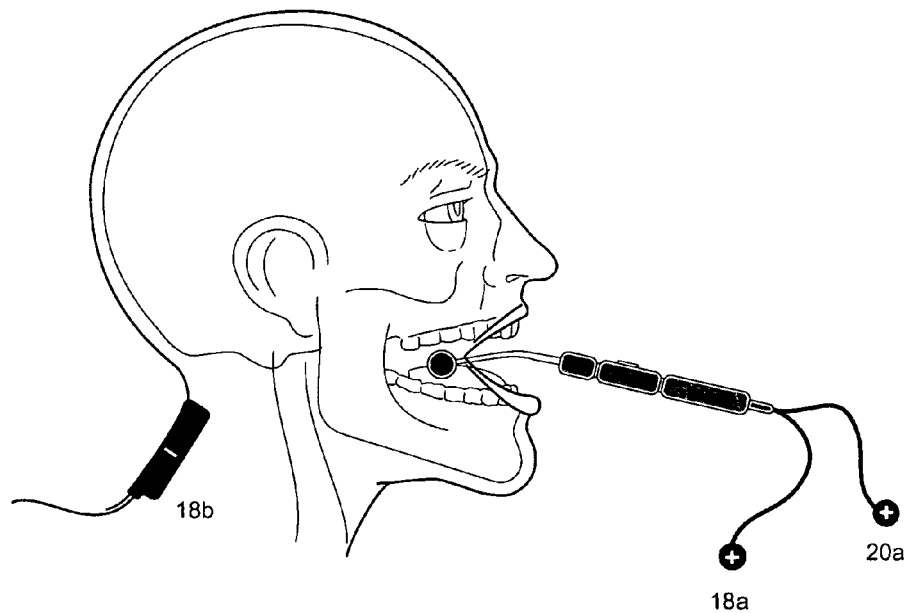
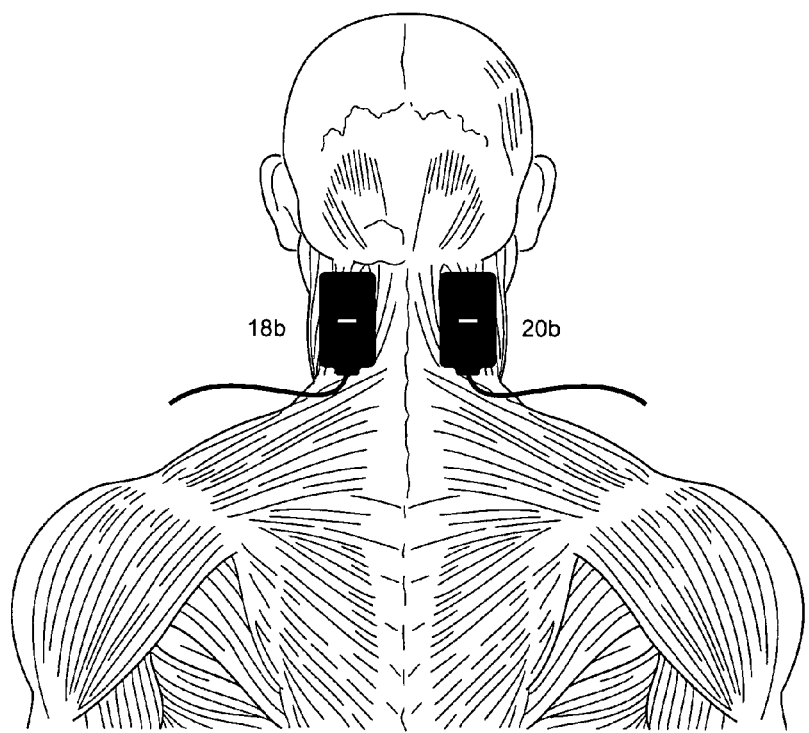

ELECTRICAL STIMULATION DEVICE AND METHOD FOR THE TREATMENT OF DYSPHAGIA

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of the Invention

The present invention is generally directed to the treatment of dysphagia, and is more specifically directed to an electrical stimulation device and method for applying a series of electrical pulses to one or more channels of electrodes in accordance with a procedure for treating dysphagia.

2. Description of Related Art

Swallowing is a complicated action whereby food is moved from the mouth through the pharynx and esophagus to the stomach. The swallowing act is usually divided into several stages that require the integrated action of the respiratory center and motor functions of multiple cranial and cervical nerves, as well as the coordination of the autonomic system.

The first stage (commonly referred to as the oral stage) involves mastication, bolus formation and bolus transfer. The food, which has been brought to the mouth, is chewed and combined with saliva to form a bolus that is moved to the back of the oral cavity and prepared for swallowing. The performance of the oral phase requires proper lip closure, cheek tensing, multidimensional tongue movement and chewing.

The second stage (commonly referred to as the oropharyngeal stage) involves the coordinated contractions of several muscles of the tongue, pharynx and larynx, whereby the bolus is moved to the back of the throat and into the esophagus. The tongue propels the bolus to the posterior mouth into the pharynx. The bolus passes through the pharynx, which involves relaxation and constriction of the walls of the pharynx, backward bending of the epiglottis, and an upward and forward movement of the larynx and trachea. The bolus is prevented from entering the nasal cavity by elevation of the soft palate and from entering the larynx by closure of the glottis and backward inclination of the epiglottis. During the oropharyngeal stage, respiratory movements are inhibited by reflex.

The third stage (commonly referred to as the esophageal stage) involves the movement of the bolus down the esophagus and into the stomach. This movement is accomplished by momentum from the prior stage, peristaltic contractions and gravity.

Dysphagia is generally defined as difficulty in swallowing. For example, dysphagia may occur when one cannot create a good lip seal/closure (which results in the leaking of the mouth contents) or ineffective tongue plunger action. Also, poor cheek tensing may result in the pocketing of food between the teeth and cheek. The patient may sometimes be unable to complete chewing due to muscle fatigue of the tongue and the muscles involved in mastication.

Classic neurologically-based dysphagia is described as a dystonia or incoordination of the oropharyngeal stage sequencing of multiple muscles controlled by the central pattern generator located in the brainstem. This level of dysphagia may manifest itself as the bolus being lodged in the throat after swallowing. The patient may even regurgitate the food or most dangerously aspirate into the airway.

Dysphagia has a variety of causes. These include obstructive/mechanical, damage to the central neuron pools (pattern generators) for swallowing following traumatic injury, or neurologic disease (as in stroke), nerve compression, neuromuscular junction atrophy or damage, and muscular atrophy and spasticity. Dysphagia may also be a sign of underlying disease of the esophagus, which may be due to strictures, gastroesophogeal reflux disease, peptic ulcers, cancer, thyroid disease, stroke, Parkinson's disease, ALS, myasthenia gravis, muscular dystrophy, muscular atrophy, torticollis, or a number of other diseases. Dysphagia may also be medication-induced.

In the past, patients suffering from dysphagia have been subjected to dietary changes or thermal and mechanical stimulation treatments to regain adequate swallowing reflexes. Thermal stimulation involves immersing a mirror or probe in ice or another cold substance and stimulating the tonsillar fossa with the cold mirror or probe. Upon such stimulation, the patient is directed to close his mouth and attempt to swallow. While dietary changes and exercise rehabilitation using thermal stimulation may be effective for treating dysphagia, some patients may require weeks or months of therapy. It is also difficult to distinguish patients who require such treatments from patients who recover spontaneously.

Electrical stimulation of various body parts has also been used in order to treat dysphagia. For example, Kaada and other researchers have reported that low-frequency transcutaneous nerve stimulation on the hands resulted in relief from dysphagia. See Kaada, *Successful treatment of esophageal dysmotility and Raynaud's phenomenon in systemic sclerosis and achalasia by transcutaneous nerve stimulation: Increase in plasma VIP concentration*, Scand. J. Gastroenterol. 1987 Nov. 22(9):1137-46; Kaada, *Systemic sclerosis: successful treatment of ulcerations, pain, Raynaud's phenomenon, calcinosis, and dysphagia by transcutaneous nerve stimulation: A case report*, Acupunct. Electrother. Res. 1984 9(1):31-44; Guelrud et al., *Transcutaneous electrical nerve stimulation decreases lower esophageal sphincter pressure in patients with achalasia*, Dig. Dis. Sci. 1991 Aug. 36(8):1029-33; Chang et al., *Effect of transcutaneous nerve stimulation on esophageal function in normal subjects—evidence for a somatovisceral reflex*, Am. J. Chin. Med. 1996 24(2):185-92. However, other researchers have found no beneficial effects associated with esophageal motility upon applying electrical simulation to the hands. See Mearin et al., *Effect of transcutaneous nerve stimulation on esophageal motility in patients with achalasia and scleroderma*, Scand. J. Gastroenterol. 1990 Oct. 25(10):1018-23.

More recently, electrical stimulation has been applied to the oral cavity for the treatment of dysphagia. See Park et al., *A pilot exploratory study of oral electrical stimulation on swallow function following stroke: an innovative technique*, Dysphagia. 1997 Summer 12(3):161-6. Other researchers have reported improved swallowing with the use of transcutaneous electrical stimulation applied to the anterior portion of the neck (i.e., the region bounded on the upper side by the mandible and on the lower side by the clavicles and the manubrium of the sternum). See Freed et al., U.S. Patent Application No. 2004/0220645 entitled "Treatment of oropharyngeal disorders by application of neuromuscular electrical stimulation"; Freed et al., U.S. Pat. No. 5,725,564; Freed et al., U.S. Pat. No. 5,891,185; Freed et al., U.S. Pat. No. 5,987,359; and Freed et al., U.S. Pat. No. 6,198,970. The Freed method may pose a safety hazard to the patient if the electrodes and stimulation are inadvertently placed over the carotid sinus (which may alter blood pressure and/or cardiac contractility). In addition, a risk occurs if the electrodes and stimulation are applied anteriorly over the laryngeal or pharyngeal muscles (which may cause a blockage of the patient's airway and cause difficulty in breathing due to electrical activation of the muscles causing a strong contraction). Further, when the electrodes are placed on the anterior neck and the chin is tucked for swallowing, the electrodes may contact each other shorting out and causing uncomfortable or dangerous surges in current. Loose skin, adipose tissue and facial hair further limit the placement and adhesion of electrodes to the target treatment area. Thus, there is a need in the art for an improved or alternative method for treating dysphagia.

BRIEF SUMMARY OF THE INVENTION

The present invention is directed to an electrical stimulation device and method for the treatment of dysphagia. In general, the electrical stimulation device includes an electronic control unit connected to one or more channels of electrodes, such as transcutaneous or percutaneous electrodes. Each channel comprises two electrodes (i.e., a relative positive electrode and a relative negative electrode), wherein one electrode is positioned in electrical contact with tissue of a target region of the patient (preferably to stimulate a motor point of one or more muscles involved in the oral, oropharyngeal and/or esophageal stages of swallowing or a combination of the swallowing stages) and the other electrode is positioned in electrical contact with tissue of a posterior neck region or a posterior thoracic region of the patient. The electronic control unit applies a series of electrical pulses to the patient through the one or more channels of electrodes in accordance with a procedure for treating dysphagia.

In the present invention, the electrodes are preferably placed on the patient in a manner that stimulates the central pattern generators associated with swallowing. In this regard, it will be appreciated that the cranial roots of the accessory nerve (XI) convey most of the fibers from the recurrent laryngeal nerve to the vagus nerve (X), which provides most of the motor fibers distributed in the pharyngeal and recurrent laryngeal branches of the vagus nerve. The activation and sequencing of these nerves are under the control of the swallowing central pattern generator associated with swallowing. The cranial root of the accessory nerve (XI) can be accessed in the posterior neck region between the C1-C4 cervical vertebrae and in the trapezius muscle (which is innervated by the spinal branch of the accessory nerve) using the relative negative electrode.

Thus, for example, in the present invention, placement of one electrode at the posterior neck region or posterior thoracic region of the patient and placement of another electrode near the buccinator, orbicularis oris, masseter, pterygoids, tongue, trapezius, median nerve, and/or first dorsal interosseous muscles of the patient will reeducate the central pattern generator associated with the various stages and related muscles involved in swallowing. The relative positive and negative electrodes contain both phases of the current and, thus, the electrode placement is generally determined by the sensitivity of the neural structures and the proximity of the nerve to the superficial tissue. Thus, the relative negative electrode is generally placed paraspinally over the accessory and spinal nerves, which are deeper and more difficult to activate than, for example, the motor points of the buccinator, orbicularis oris, masseter, pterygoids, tongue, trapezius, median nerve, and/or first dorsal interosseous muscles.

In one aspect, stimulation of the cervical paraspinal muscles with the relative negative electrode and stimulation of the motor point of the right and/or left buccinator and/or orbicularis oris muscle with the relative positive electrode has been shown to improve swallowing during the oral phase, especially that associated with proper lip seal and tongue movement.

In another aspect, stimulation of the cervical paraspinal muscles with the relative negative electrode and stimulation of the motor point of the right and/or left masseter muscle and/or pterygoid muscle with the relative positive electrode has been shown to improve swallowing during the oral phase, especially that involving chewing.

In still another aspect, stimulation of the cervical paraspinal muscles with the relative negative electrode and stimulation of the motor point of the tongue with the relative positive electrode has been shown to improve the oral and oropharyngeal phases of swallowing associated with multidimensional movement of the bolus to the pharynx by the tongue.

In yet a further aspect, stimulation of the cervical paraspinal muscles with the relative negative electrode and stimulation of the motor point of the right and/or left trapezius muscle with the relative positive electrode has been shown to improve the oropharyngeal phase of swallowing.

In still another aspect, stimulation of the cervical paraspinal muscles with the relative negative electrode and stimulation of the left and/or right median nerves in the vicinity of the anterior surface of the wrist and/or stimulation of the motor point of the left and/or right first dorsal interosseous muscle with the relative positive electrode has been shown to improve the oropharyngeal and esophageal phases of swallowing. This stimulation is thought to modulate the gag reflex in patients who may have hypersensitivity or neurologic inhibition of the gag reflex due to central pattern generator damage in which case the stimulation reeducates the correct pattern for the reflex. This tracks the innervation of the cervical esophagus at the C1-C8 cervical afferent and efferent nerves and spinal interneuron loops located at the levels of the C1-C7 spinal vertebrae. In addition, there is supplementary accessible innervation through the median and ulnar nerves at the first dorsal interosseous muscle through the nerve roots located at the levels of the C5-C7 vertebrae.

In still another aspect, stimulation of the thoracic paraspinal muscles with the relative negative electrode and stimulation of the left and/or right median nerves in the vicinity of the anterior surface of the wrist and/or stimulation of the motor point of the left and/or right first dorsal interosseous muscle with the relative positive electrode has been shown to improve the oropharyngeal and esophageal phases. Again, the therapy is thought to modulate the gag reflex due to central pattern generator abnormalities. This tracks the innervation of the mid to lower esophagus at the T4-T6 thoracic afferents, interneurons, and efferents with suprasegmental (cervical and brainstem) input.

Lastly, stimulation of the cervical paraspinal muscles (e.g., the C1-C4 or C5-C7 cervical vertebrae) with the relative negative electrode and stimulation of the thoracic paraspinal muscles (e.g., the T4-T6 thoracic vertebrae) has been shown to improve the esophageal phase of swallowing.

The series of electrical pulses applied to the one or more channels of electrodes may comprise a variety of different types of pulse train patterns. For example, a plurality of cycles of a biphasic sequential or overlapping pulse train pattern may be used, in which a first phase of electrical pulses is applied to a first channel of electrodes and a second phase of electrical pulses is applied to a second channel of electrodes. Using the biphasic sequential pulse train pattern, the second phase of electrical pulses commences after termination of the first phase of electrical pulses such that there is a time delay therebetween. Using the biphasic overlapping pulse train pattern, the second phase of electrical pulses commences before termination of the first phase of electrical pulses such that there is an overlap therebetween.

In another example, a plurality of cycles of a triphasic sequential or overlapping pulse train pattern may be used, in which a first phase of electrical pulses is applied to a first channel of electrodes, a second phase of electrical pulses is applied to a second channel of electrodes, and a third phase of electrical pulses is applied to the first channel of electrodes. Using the triphasic sequential pulse train pattern, the second phase of electrical pulses commences after termination of the first phase of electrical pulses such that there is a time delay therebetween and, similarly, the third phase of electrical pulses commences after termination of the second phase of electrical pulses such that there is a time delay therebetween. Using the triphasic overlapping pulse train pattern, the second phase of electrical pulses commences before termination of the first phase of electrical pulses such that there is an overlap therebetween and, similarly, the third phase of electrical pulses commences before termination of the second phase of electrical pulses such that there is an overlap therebetween.

In yet another example, the series of electrical pulses comprises a functional pulse train pattern applied to one or more channels of electrodes. In this example, the pulse train pattern attempts to mimic the electrical sequencing of particular muscles involved in swallowing (e.g., the buccinator muscles, the orbicularis oris muscles, the masseter muscles, the pterygoid muscles, the tongue, and the pharyngeal and laryngeal muscles) during normal functioning activity.

In a further example, the series of electrical pulses comprises a low-frequency pulse train pattern applied to one or more channels of electrodes, wherein the individual electrical pulses are generated at a frequency of between 0.1 Hz and 200 Hz to selectively generate the relative selective production neurotransmitters and modulators (endorphins, dynorphins, enkephalin, and serotonin, etc.) based on the frequency selected. Stimulation at specific frequencies is believed to have beneficial effects in the treatment of dysphagia due to the normalization of hyperactive sensory inputs (which play a role in the re-education of the central pattern generators) or triggering descending inhibition to reduce overactive muscle tone and/or spasticity. The use of a single frequency of stimulation may be most effective in targeting a single mechanism of inhibition that may be dysfunctional.

Alternatively, a frequency-sequenced pulse burst train pattern may be applied to one or more channels of electrodes, wherein different sequences of modulated electrical pulses are generated at different burst frequencies. Preferably, the different burst frequencies are selected so as to generate the simultaneous production of endorphins, dynorphins, enkephalin, and serotonin during each of the respective sequences, which is believed to have beneficial effects in the treatment of dysphagia due to the normalization of hyperactive sensory inputs (which play a role in the re-education of the central pattern generators) or triggering descending inhibition to reduce overactive muscle tone and/or spasticity. The combined effect of the generation of multiple inhibitory or excitatory neurotransmitters may provide a more powerful effect than a single neurotransmitter for use in more difficult cases or as a more generalized approach as compared to the single frequency method.

BRIEF DESCRIPTION OF THE DRAWINGS

The present invention will be described in greater detail in the following detailed description of the invention with reference to the accompanying drawings that form a part hereof, in which:

FIG. 1 is a block diagram of an electrical stimulation device that may be used in accordance with the method of the present invention;

FIG. 3C illustrates a method for treating dysphagia in a patient by applying electrical stimulation in accordance with a third exemplary embodiment of the present invention, in which the tongue muscles and the cervical paraspinal muscles of the patient are stimulated;

DETAILED DESCRIPTION OF THE INVENTION

Figure 2A:
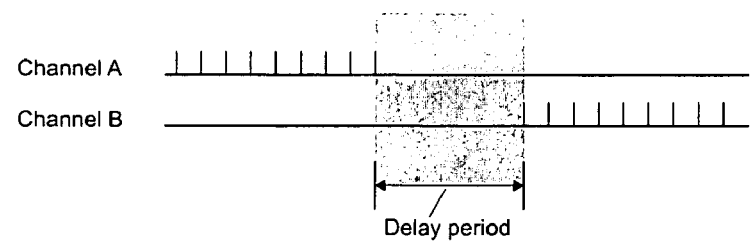
FIG. 2A is a timing diagram of a biphasic sequential pulse train pattern that may be applied to the output channels of the electrical stimulation device of FIG. 1.

The present invention is directed to an electrical stimulation device and method for the treatment of dysphagia. As used herein, the term "electrical stimulation" refers to the passing of various types of current to a patient through transcutaneous or percutaneous electrodes, and includes indirect nerve and/or muscle activation by stimulation of the nerves innervating the sensor (cutaneous and position sensors) and muscle fibers associated with central pattern generator inputs or inhibitory mechanism and stimulation of motor efferent fibers which activate the muscles associated with swallowing.

Examples of the types of electrical stimulation that may be used include, but are not limited to, Patterned Electrical Neuromuscular Stimulation (PENS), Transcutaneous Electrical Nerve Stimulation (TENS), Neuromuscular Electrical Stimulation (NMES), and Interferential Current (IFC), Percutaneous Electrical Muscle Stimulation (PEMS), Percutaneous Electrical Nerve Stimulation (PENS), which may use alternating or modulated alternating current waveforms, asymmetrical or symmetrical biphasic pulsed current waveforms and monophasic pulsed current waveforms. Of course, one skilled in the art will appreciate that other types of electrical stimulation may also used in accordance with the present invention.

As used herein, the term "posterior neck region" refers to the region or portion thereof generally bounded by the occiput and the C1 to C7 cervical vertebrae and extending along the cervical paraspinal muscles and the trapezius muscle of the patient with afferent and efferent innervation to the C1-C8 spinal nerves.

As used herein, the term "posterior thoracic region" refers to the region generally bounded by the T1 to T6 thoracic spinous process line and extending along the thoracic paraspinal muscles of the patient to the medial border of the scapulae.

As used herein, the term "motor point" refers to an area of tissue that can be electrically stimulated by lower levels of electricity compared to surrounding areas. The motor point overlies the innervation zone of a muscle where the motor nerve endings are concentrated or where the nerve trunk enters the muscle. The motor point is often used as a placement site for surface electrodes used to stimulate the muscle.

As used herein, the term "tissue" refers to an aggregation of morphologically similar cells and associated intercellular matter acting together to perform one or more specific functions in the body, including epithelial, connective, muscle, and neural tissue.

As used herein, the term "treatment" refers to the treatment of dysphagia in a patient, such as a mammal (particularly a human), which includes preventing, ameliorating, suppressing, or alleviating one ore more of the symptoms of dysphagia.

Referring to FIG. 1, an exemplary embodiment of an electrical stimulation device that may be used in accordance with the method of the present invention is designated generally as reference numeral 10. Electrical stimulation device 10 generally comprises an electronic control unit 12 with a plurality of output connectors 14, 16, which are connected to a plurality of output cables 18, 20 and associated electrode pairs 18a, 18b and 20a, 20b, respectively. Although two output connectors 14, 16 are shown in FIG. 1, it should be understood that electronic control unit 12 may include any number of output connectors (such as one, two, six or eight output connectors) in accordance with the present invention.

Output cables 18, 20 each comprise any suitable type of insulated conductive cable, such as a coaxial cable. In the illustrated embodiment, output cable 18 includes a back section 22 with a connector 24 (such as a male jack) that attaches to output connector 14, and a front section 26 that splits into a first split end 26a and a second split end 26b. Similarly, output cable 20 includes a back section 28 with a connector 30 (such as a male jack) that attaches to output connector 16, and a front section 32 that splits into a first split end 32a and a section split end 32b. Of course, it should be understood that each of output cables 18, 20 could alternatively be manufactured out of two separate leads (instead of having a front section with split ends). In addition, output cables 18, 20 could be connected directly to electronic control unit 12 without the use of connectors.

As can be seen in FIG. 1, electrodes 18a, 18b are attached to split ends 26a, 26b of output cable 18, respectively. Similarly, electrodes 20a, 20b are attached to split ends 32a, 32b of output cable 20, respectively. As such, output cable 18 and electrodes 18a, 18b together form a first output channel (referred to hereinafter as "channel A"), and output cable 20 and electrodes 20a, 20b together form a second output channel (referred to hereinafter as "channel B"). Although two channels are shown in FIG. 1, it should be understood that any number of channels may be used in accordance with the present invention (provided, of course, that the number of channels corresponds to the number of output connectors of electronic control unit 12).

In the illustrated example, electrodes 18a and 20a each comprise a relative positive electrode, and electrodes 18b and 20b each comprise a relative negative electrode. As will be described in greater detail hereinbelow, each of the electrical pulses applied to electrodes 18a, 18b and electrodes 20a, 20b may comprise, for example, a monophasic waveform (which has absolute polarity), a biphasic asymmetric waveform (which has relative polarity), or a biphasic symmetric waveform (which has no polarity). Thus, as used herein, the term "positive electrode" refers to a relative positive electrode and the term "negative electrode" refers to a relative negative electrode (regardless of whether the electrical pulse comprises a monophasic waveform, an asymmetric biphasic waveform, or a symmetric biphasic waveform (which behaves like the relative positive or relative negative electrode during each phase of the waveform)).

Electrodes 18a, 18b and 20a, 20b are each adapted to be positioned in electrical conduct with tissue of selected regions of a patient, as will be described in greater detail hereinbelow with reference to FIGS. 3A-3G. In the illustrated embodiment, each of electrodes 18a, 18b and 20a, 20b comprises a transcutaneous electrode having a surface electrode pad that may be placed on the skin of a patient. As is known in the art, each of electrodes 18a, 18b and 20a, 20b may be formed of metal or some other physiologically acceptable conductive material and may take on a variety of different sizes and shapes. Of course, one or more of electrodes 18a, 18b and 20a, 20b may alternatively comprise a percutaneous electrode, such as a needle electrode, or any other type of suitable electrode in accordance with the present invention.

Electronic control unit 12 also includes internal circuitry (not shown) for selectively generating a series of electrical pulses in accordance with a procedure for treating dysphagia. The series of electrical pulses generated by the circuitry are provided at output connectors 14, 16 and, as such, may be applied to a patient through channel A and/or channel B. The series of electrical pulses may comprise a variety of different types of pulse train patterns, such as: a plurality of cycles of a biphasic sequential pulse train pattern; a plurality of cycles of a biphasic overlapping pulse train pattern; a plurality of cycles of a triphasic sequential pulse train pattern; a plurality of cycles of a triphasic overlapping pulse train pattern; a functional pulse train pattern; a low-frequency pulse train pattern; or a frequency-sequenced pulse burst train pattern. Each of these pulse train patterns will be described in detail hereinbelow with reference to FIGS. 2A-2H. One skilled in the art will understand that a variety of different circuit configurations may be used to generate the various pulse train patterns, such as the circuitry described in Palermo U.S. Pat. No. 5,562,718, which is incorporated herein by reference.

A variety of different electrical stimulation devices may be used and/or adapted for use in accordance with the present invention. For example, one could easily incorporate the protocols disclosed herein into the Omnistim® FX² patterned electrical neuromuscular stimulator or the Omnistim® FX² Pro patterned electrical neuromuscular stimulator, both of which are sold by the assignee of the present application. Of course, other types of electrical stimulation devices could also be used, which are generally available in the industry.

Referring now to FIGS. 2A-2H, examples of the various types of pulse train patterns that may be used in accordance with the present invention will now be described hereinbelow. Each of the pulse train patterns is comprised of a series of individual electrical pulses arranged into a particular pattern. Each of the electrical pulses may comprise either a monophasic or biphasic waveform, which may be, for example, asymmetric, symmetric, square, sinusoidal, and the like. Preferably, each of the electrical pulses comprises a biphasic asymmetric square wave having a pulse duration that ranges between 30 microseconds and 100 microseconds during the positive and negative phases and a current amplitude that typically ranges between 25 milliamps and 140 milliamps.

It has been found that electrical pulses having a short pulse duration and high current amplitude selectively trigger p-type calcium channels (preferably having a pulse duration of 30-100 microseconds and a current amplitude of 25-140 milliamps). Activation of p-type calcium channels will in turn trigger the release of nerve growth factor ("NGF") to sustain axon regeneration and repair. This repeated p-type calcium channel activation increases the calcium pool at the neuromuscular junction, which facilitates enhanced muscle recruitment. Twitch contractions may increase in intensity during the treatment even though the stimulation output is not increased as observed empirically. This additional calcium at the neuromuscular junction lasts for several hours post-treatment, which facilitates voluntary movement. See Regeneron Corp. (Tarrytown N.Y.) Neural stimulation effects presentation, Society for Neuroscience, San Diego 1998 (short and long term nerve growth potentiation using repetitive electric stimulation).

Biphasic Sequential Pulse Train Pattern

Referring to FIG. 2A, electrical stimulation device 10 may be used to apply a plurality of cycles of a biphasic sequential pulse train pattern to a patient. In a typical biphasic sequential pulse train pattern, a first phase of electrical pulses is applied to channel A and a second phase of electrical pulses is applied to channel B with a delay period therebetween.

In the illustrated example, the first phase of electrical pulses is applied to channel A for approximately 60 milliseconds to 120 milliseconds (and most preferably for 100 milliseconds). At the conclusion of the first phase of electrical pulses, there is a delay period of approximately 0 milliseconds to 100 milliseconds (and most preferably 80 milliseconds) before the second phase of electrical pulses is applied to channel B. Then, the second phase of electrical pulses is applied to channel B for approximately 60 milliseconds to 120 milliseconds (and most preferably for 100 milliseconds). The frequency of the individual electrical pulses in each phase is approximately 30 Hz to 100 Hz (and most preferably 50 Hz).

The biphasic sequential pulse train pattern described above may be repeated approximately every 0.33 seconds (3 Hz) to 3 seconds (0.33 Hz), depending on the stage of swallowing being treated. Preferably, the pulse train pattern is applied to the patient for a total treatment time of approximately 10 minutes to 30 minutes (and most preferably for 20 minutes), as desired for a particular treatment.

Biphasic Overlapping Pulse Train Pattern

Figure 2B:
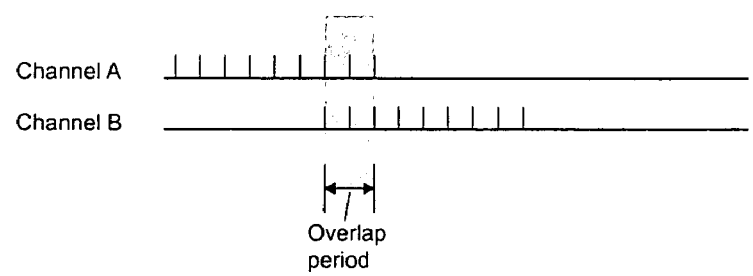
FIG. 2B is a timing diagram of a biphasic overlapping pulse train pattern that may be applied to the output channels of the electrical stimulation device of FIG. 1.

Referring to FIG. 2B, electrical stimulation device 10 may also be used to apply a plurality of cycles of a biphasic overlapping pulse train pattern to a patient. In a typical biphasic overlapping pulse train pattern, a first phase of electrical pulses is applied to channel A and a second phase of electrical pulses is applied to channel B with an overlap period therebetween.

In the illustrated example, the first phase of electrical pulses is applied to channel A for approximately 60 milliseconds to 120 milliseconds (and most preferably for 100 milliseconds). When the first phase of electrical pulses has reached a time period of between 40 milliseconds and 100 milliseconds (and most preferably 80 milliseconds), the second phase of electrical pulses is applied to channel B for approximately 60 milliseconds to 120 milliseconds (and most preferably for 100 milliseconds). Thus, there is an overlap period of approximately 20 milliseconds to 80 milliseconds (and most preferably 20 milliseconds) during which both channel A and channel B are providing electrical stimulation to the patient. The frequency of the individual electrical pulses in each phase is approximately 30 Hz to 100 Hz (and most preferably 50 Hz).

The biphasic overlapping pulse train pattern described above may be repeated approximately every 0.33 seconds (3 Hz) to 3 seconds (0.33 Hz), depending on the stage of swallowing being treated. Preferably, the pulse train pattern is applied to the patient for a total treatment time of approximately 10 minutes to 60 minutes (and most preferably 20 minutes), as desired for a particular treatment.

Triphasic Sequential Pulse Train Pattern

Figure 2C:
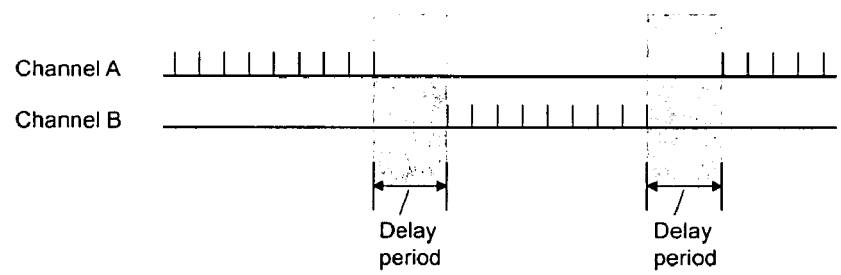
FIG. 2C is a timing diagram of a triphasic sequential pulse train pattern that may be applied to the output channels of the electrical stimulation device of FIG. 1.

Referring to FIG. 2C, electrical stimulation device 10 may also be used to apply a plurality of cycles of a triphasic sequential pulse train pattern to a patient. In a typical triphasic sequential pulse train pattern, a first phase of electrical pulses is applied to channel A, a second phase of electrical pulses is applied to channel B, and a third phase of electrical pulses is applied to channel A, wherein there is a delay period between the first and second phases of electrical pulses and another delay period between the second and third phases of electrical pulses.

In the illustrated example, the first phase of electrical pulses is applied to channel A for approximately 60 milliseconds to 120 milliseconds (and most preferably for 100 milliseconds). At the conclusion of the first phase of electrical pulses, there is a delay period of approximately 0 milliseconds to 100 milliseconds (and most preferably 80 milliseconds) before the second phase of electrical pulses is applied to channel B. Then, the second phase of electrical pulses is applied to channel B for approximately 60 milliseconds to 120 milliseconds (and most preferably for 100 milliseconds). At the conclusion of the second phase of electrical pulses, there is a delay period of approximately 0 milliseconds to 100 milliseconds (and most preferably 80 milliseconds) before the third phase of electrical pulses is applied to channel A. Then, the third phase of electrical pulses is applied to channel A for approximately 36 milliseconds to 72 milliseconds (and most preferably for 60 milliseconds). The frequency of the individual electrical pulses in each phase is approximately 30 Hz to 100 Hz (and most preferably 50 Hz).

The triphasic sequential pulse train pattern described above may be repeated approximately every 0.33 seconds (3 Hz) to 3 seconds (0.33 Hz), depending on the stage of swallowing being treated. Preferably, the pulse train pattern is applied to the patient for a total treatment time of approximately 10 minutes to 60 minutes (and most preferably 20 minutes), as desired for a particular treatment.

Figure 2D:
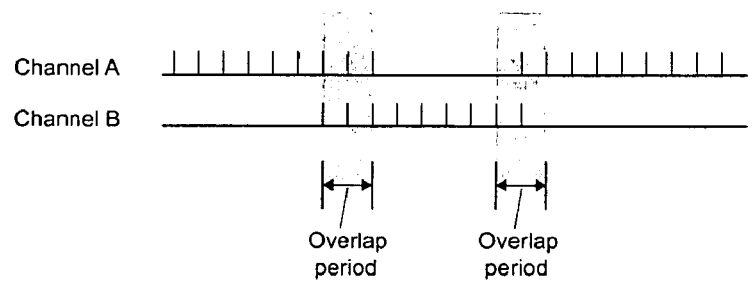
FIG. 2D is a timing diagram of a triphasic overlapping pulse train pattern that may be applied to the output channels of the electrical stimulation device of FIG. 1.

Referring to FIG. 2D, electrical stimulation device 10 may also be used to apply a plurality of cycles of a triphasic overlapping pulse train pattern to a patient. In a typical triphasic overlapping pulse train pattern, a first phase of electrical pulses is applied to channel A, a second phase of electrical pulses is applied to channel B, and a third phase of electrical pulses is applied to channel A, wherein there is an overlap period between the first and second phases of electrical pulses and another overlap period between the second and third phases of electrical pulses.

In the illustrated example, the first phase of electrical pulses is applied to channel A for approximately 60 milliseconds to 120 milliseconds (and most preferably for 100 milliseconds). When the first phase of electrical pulses has reached a time period of between 40 milliseconds and 100 milliseconds (and most preferably 80 milliseconds), the second phase of electrical pulses is applied to channel B for approximately 60 milliseconds to 120 milliseconds (and most preferably 100 milliseconds). Thus, there is an overlap period of approximately 0 milliseconds to 100 milliseconds (and most preferably 20 milliseconds) during which both channel A and channel B are providing electrical stimulation to the patient. When the second phase of electrical pulses has reached a time period of between 40 milliseconds and 100 milliseconds (and most preferably 80 milliseconds), the third phase of electrical pulses is applied to channel A for approximately 36 milliseconds to 72 milliseconds (and most preferably 60 milliseconds) (i.e., the third phase of electrical pulses has a shorter time duration than that of the first phase of electrical pulses). Thus, there is an overlap period of approximately 0 milliseconds to 72 milliseconds (and most preferably 20 milliseconds) during which both channel B and channel A are providing electrical stimulation to the patient. The frequency of the individual electrical pulses in each phase is approximately 30 Hz to 100 Hz (and most preferably 50 Hz).

The triphasic overlapping pulse train pattern described above may be repeated approximately every 0.33 seconds (3 Hz) to 3.0 seconds (0.33 Hz), depending on the stage of swallowing being treated. Preferably, the pulse train pattern is applied to the patient for a total treatment time of approximately 10 minutes to 60 minutes (and most preferably 20 minutes), as desired for a particular treatment.

Functional Pulse Train Pattern

Electrical stimulation device 10 may also be used to apply a functional pulse train pattern to a patient. The functional pulse train pattern is applied to channel A and channel B (or to additional channels) so as to mimic the electrical sequencing of particular muscles involved in swallowing during normal functioning activity. One skilled in the art will understand that the functional pulse train pattern for a particular functioning activity (e.g., chewing, moving the bolus or swallowing) may be obtained through the use of an electromyographic (EMG) recording device. The sequence of firing of the muscles, firing frequencies, and the duration and frequency of the firing of the muscles may thus be determined for standardized healthy normal subjects and may then be programmed into the appropriate stimulation pattern. Preferably, the functional pulse train pattern is applied to the patient for a total treatment time of approximately 10 minutes to 60 minutes (and most preferably 20 minutes), as desired for a particular treatment.

Low-Frequency Pulse Train Pattern

Figure 2E:
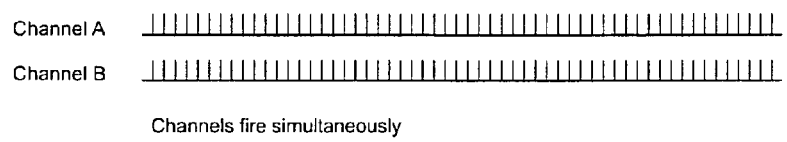
FIG. 2E is a timing diagram of a low-frequency pulse train pattern that may be applied to the output channels of the electrical stimulation device of FIG. 1.

Referring to FIG. 2E, electrical stimulation device 10 may also be used to apply a low-frequency pulse train pattern to a patient. The low-frequency pulse train pattern may be applied to channel A and/or channel B, wherein the individual electrical pulses are generated on each channel at a frequency of between 0.1 Hz and 200 Hz. Generally, the frequency of the electrical pulses is selected in order to provide the desired response and release of stimulatory or inhibitory neurotransmitters centrally and spinally while providing the greatest comfort to the patient. If channel A and channel B are both used, the low-frequency pulse train pattern may be applied simultaneously to channel A and channel B, or, a different frequency may be applied on each channel to a different area associated with various phases of swallowing. Preferably, the low-frequency pulse train pattern is applied to the patient for a total treatment time of approximately 5 minutes to 60 minutes (and most preferably 20 minutes), as desired for a particular treatment.

Frequency-Sequenced Pulse Burst Train Pattern

Figure 2F:
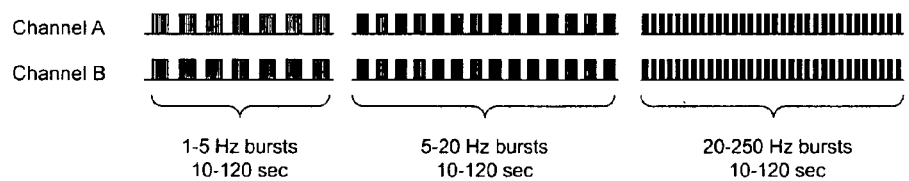
FIG. 2F is a timing diagram of a first frequency-sequenced pulse burst train pattern that may be applied to the output channels of the electrical stimulation device of FIG. 1.
Figure 2G:
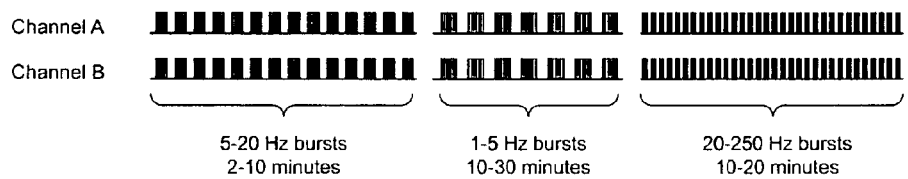
FIG. 2G is a timing diagram of a second frequency-sequenced pulse burst train pattern that may be applied to the output channels of the electrical stimulation device of FIG. 1.
Figure 2H:
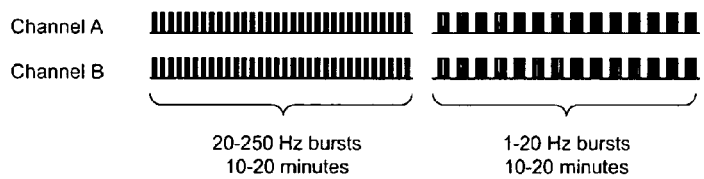
FIG. 2H is a timing diagram of a third frequency-sequenced pulse burst train pattern that may be applied to the output channels of the electrical stimulation device of FIG. 1.

Referring to FIGS. 2F-2H, electrical stimulation device 10 may also be used to apply a frequency-sequenced pulse burst train pattern to a patient. The frequency-sequenced pulse burst train pattern may be applied to channel A and/or channel B, wherein different sequences of modulated electrical pulses are generated at different frequencies. Preferably, the different burst frequencies are selected so as to selectively generate the production of endorphin, dynorphin, and enkephalin/serotonin during each of the respective sequences, which is believed to have beneficial effects in the treatment of dysphagia.

In the example shown in FIG. 2F, the frequency-sequenced pulse burst train pattern has a carrier frequency of 500 Hz to 100,000 Hz with a first sequence of modulated electrical pulses generated at a burst frequency of approximately 0.1 Hz to 5 Hz for a duration of approximately 1 seconds to 120 seconds, a second sequence of modulated electrical pulses generated at a burst frequency of approximately 5 Hz to 20 Hz for a duration of approximately 1 seconds to 120 seconds, and a third sequence of modulated electrical pulses generated at a burst frequency of approximately 20 Hz to 250 Hz for a duration of approximately 1 seconds to 120 seconds. Preferably, the frequency-sequenced pulse burst train pattern is applied to the patient for a total treatment time of approximately 1 minute to 60 minutes. Using this therapy, the patient begins to receive the effects of all of the neurotransmitters relatively quickly as the frequencies cycle through rapidly. This therapy is also very comfortable and moderately aggressive.

In the example shown in FIG. 2G, the frequency-sequenced pulse burst train pattern has a carrier frequency of 500 Hz to 100,000 Hz with a first sequence of modulated electrical pulses generated at a burst frequency of approximately 5 Hz to 20 Hz for a duration of approximately 1 minute to 10 minutes, a second sequence of modulated electrical pulses generated at a burst frequency of approximately 0.1 Hz to 5 Hz for a duration of approximately 1 minute to 30 minutes, and a third sequence of modulated electrical pulses generated at a burst frequency of approximately 20 Hz to 250 Hz for a duration of approximately 1 minute to 20 minutes. Preferably, the frequency-sequenced pulse burst train pattern is applied to the patient for a total treatment time of approximately 3 minutes to 50 minutes. This therapy is the most aggressive and least tolerated but provides the longest lasting effect. The initial effect is dynorphin (5-20 Hz), followed by endorphin (1-5 Hz), and then by enkephalin/serotonin (20-250 Hz). Since it takes 15 to 30 minutes to activate endorphin and only 5-10 minutes to activate enkephalin/serotonin, both are present at the completion of the treatment for maximum effect.

In the example shown in FIG. 2H, the frequency-sequenced pulse burst train pattern has a carrier frequency of 500 Hz to 100,000 Hz with a first sequence of modulated electrical pulses generated at a burst frequency of approximately 20 Hz to 250 Hz for a duration of approximately 1 minute to 20 minutes, and a second sequence of modulated electrical pulses generated at a burst frequency of approximately 0.1 Hz to 20 Hz for a duration of approximately 1 minute to 20 minutes. Preferably, the frequency-sequenced pulse burst train pattern is applied to the patient for a total treatment time of approximately 20 minutes to 40 minutes. This therapy is the least aggressive and best tolerated but provides the shortest lasting effect. The initial effect is enkephalin/serotonin (20-250 Hz) followed by endorphin (1-20 Hz). Since it takes about 15-30 minutes to activate endorphin and only about 5-10 minutes to activate enkephalin/serotonin, both are present at the completion of the treatment. However, the enkephalin/serotonin has begun to deplete as it has a relatively short half life (15 minutes to 2 hours) compared to endorphin (2-6 hours). Stimulation at higher frequencies is better tolerated and thus more appropriate to start with for more sensitive patients.

Referring now to FIGS. 3A-3E, electrodes 18a, 18b and 20a, 20b are each adapted to be positioned in electrical contact with tissue of selected regions of a patient. The selected regions are preferably those that will assist in programming the central pattern generators associated with swallowing. These central pattern generators are neuronal ensembles located in the brain stem capable of producing the basic spatiotemporal patterns underlying "automatic" swallowing movements in the absence of peripheral feedback. In the present invention, the muscle contractions produced by the pulse train patterns provide afferent inputs or efferent stimulation that assist in retraining of the central nervous system and spinal motor loops to promote normal muscle function. In particular, it has been found that stimulation of the buccinator, orbicularis oris, masseter, trapezius, median nerve, first dorsal interosseous muscle and mid thoracic paraspinals in conjunction with the posterior neck region or posterior thoracic region may assist in retraining the central pattern generators associated with swallowing.

It will be appreciated that when multiple channels are used (e.g., in the case of biphasic and triphasic pulse patterns), the first pulse pattern is preferably applied to the muscle most seriously affected. For example, if a patient complains of muscle weakness in chewing primarily on the right side of the body, the motor point of the masseter muscle on the right side of the patient's body preferably receives the pulse pattern on channel A and the motor point of the masseter muscle on the left side of the patient's body preferably receives the pulse pattern on channel B.

The dysphagia treatment methods of the present invention are well-adapted to be used with other conventional therapies for dysphagia treatment, including changing the diet (such as eating thickened liquids or thin liquids, depending on the type of dysphagia), swallowing exercises, changes in body posture, strengthening exercises, and even surgery. Medications useful for treating dysphagia include, but are not limited to, nitrates (e.g., nitroglycerin, isosorbide), anticholinergics (e.g., dicyclomine, hyoscyamine sulfate), calcium-channel blockers (e.g., nifedipine, diltiazem), sedatives/antidepressants (e.g., diazepam, trazodone, doxepin), smooth-muscle relaxants (e.g., hydralazine), and antacids (e.g., cimetidine, ranitidine, nizatidine, famotidine, omeprazole, lansoprazole, metoclopramide).

While several exemplary embodiments of the present invention are discussed below, those skilled in the art will readily appreciate that various modifications may be made to these embodiments, and the invention is not limited to the specific electrode placements and pulse train patterns described therein.

FIRST EXEMPLARY EMBODIMENT

Figure 3A:
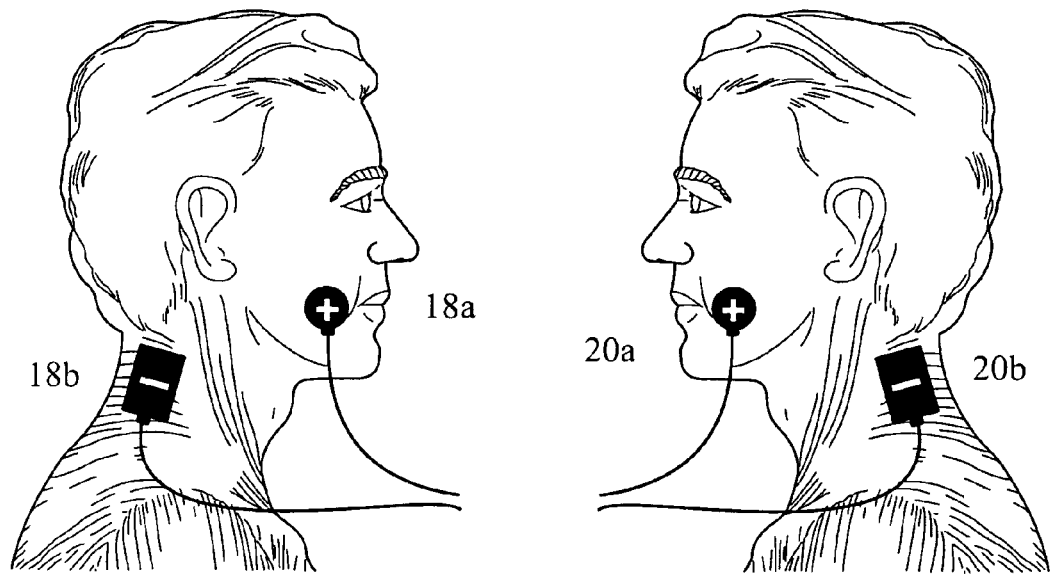
FIG. 3A illustrates a method for treating dysphagia in a patient by applying electrical stimulation in accordance with a first exemplary embodiment of the present invention, in which the buccinator and/or obicularis oris muscles and the cervical paraspinal muscles of the patient are stimulated.

In a first exemplary embodiment of the present invention, as generally illustrated in FIG. 3A, a pair of electrodes is positioned in electrical contact with the patient's tissue in order to provide electrical stimulation to one or more of the face muscles used to create proper lip seal during swallowing and to the muscles associated with the posterior neck region. A second pair of electrodes is positioned bilaterally in a similar manner.

More specifically, as shown in FIG. 3A, a first electrode 18a is positioned in electrical contact with tissue to stimulate a motor point of the patient's buccinator muscle and/or orbicularis oris muscle. Most preferably, first electrode 18a comprises a surface electrode that is positioned on the patient's skin along the distal corner of the patient's mouth. A second electrode 18b is positioned is electrical contact with tissue to stimulate the patient's cervical paraspinal muscles. Most preferably, second electrode 18b comprises a surface electrode that is positioned on the patient's skin in the posterior neck region just lateral to the one or more of the cervical vertebrae, most preferably near the C1, C2, C3 and/or C4 cervical vertebrae. Another pair of electrodes 20a, 20b is provided bilaterally in a similar position as generally illustrated in FIG. 3A.

In this exemplary embodiment, the pulse train pattern comprises a biphasic overlapping pulse train pattern having the following parameters:

Pulse duration of individual electrical pulses: 50-70 microseconds

Current amplitude of individual electrical pulses: 25-70 milliamps

Duration of first phase: 100 milliseconds

Duration of overlap: 20 milliseconds

Duration of second phase: 100 milliseconds

Frequency of pulse train pattern: 0.6 seconds

Total treatment time: 20 minutes

Total number of treatments: 18 (over six weeks)

Frequency of individual electrical pulses (in each phase): 50 hertz

SECOND EXEMPLARY EMBODIMENT

Figure 3B:
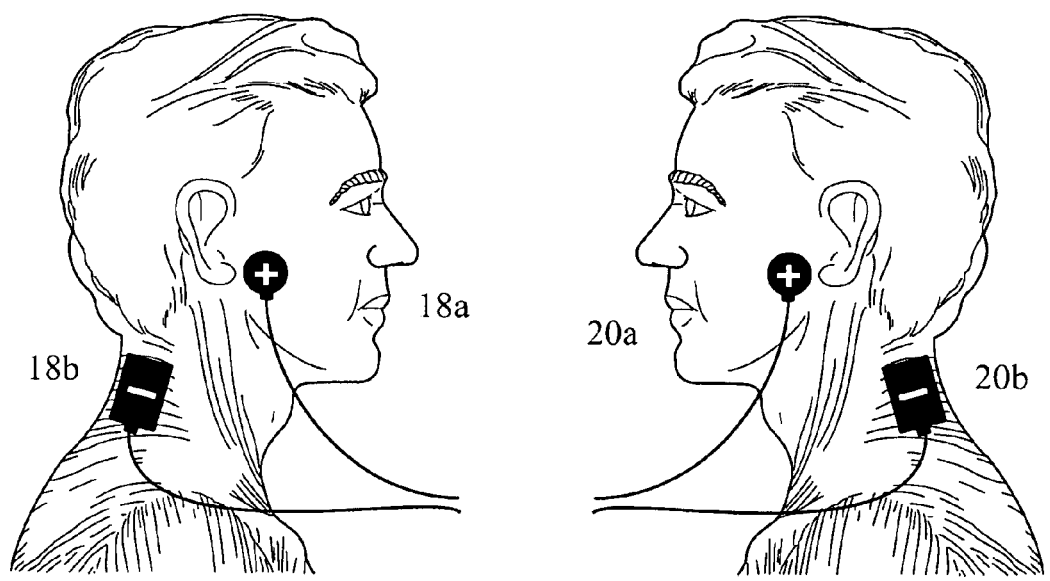
FIG. 3B illustrates a method for treating dysphagia in a patient by applying electrical stimulation in accordance with a second exemplary embodiment of the present invention, in which the masseter and/or pterygoid muscles and the cervical paraspinal muscles of the patient are stimulated.

In a second exemplary embodiment of the present invention, as generally illustrated in FIG. 3B, a pair of electrodes is positioned in electrical contact with the patient's tissue in order to provide electrical stimulation to one or more of the face muscles used to chew during swallowing and to the muscles associated with the posterior neck region. A second pair of electrodes is positioned bilaterally in a similar manner.

More specifically, as shown in FIG. 3B, a first electrode 18a is positioned in electrical contact with tissue to stimulate a motor point of the patient's masseter muscle and/or pterygoid muscle (medial and/or lateral). Most preferably, first electrode 18a comprises a surface electrode that is positioned on the patient's skin along the jaw about one inch anterior to the lower angle of the mandible at the prominence of the masseter muscle. A second electrode 18b is positioned is electrical contact with tissue to stimulate the patient's cervical paraspinal muscles. Most preferably, second electrode 18b comprises a surface electrode that is positioned on the patient's skin in the posterior neck region just lateral to the one or more of the cervical vertebrae, most preferably near the C1, C2, C3 and/or C4 cervical vertebrae. Another pair of electrodes 20a, 20b is provided bilaterally in a similar position as generally illustrated in FIG. 3B.

In this exemplary embodiment, the pulse train pattern comprises a biphasic overlapping pulse train pattern having the following parameters:

Pulse duration of individual electrical pulses: 50-70 microseconds

Current amplitude of individual electrical pulses: 20-70 milliamps

Duration of first phase: 100 milliseconds

Duration of overlap: 20 milliseconds

Duration of second phase: 100 milliseconds

Frequency of pulse train pattern: 0.6 seconds

Total treatment time: 20 minutes

Total number of treatments: 36

Frequency of individual electrical pulses (in each phase): 50 hertz

THIRD EXEMPLARY EMBODIMENT

In a third exemplary embodiment of the present invention, as generally illustrated in FIG. 3C, a probe is positioned in electrical contact with the patient's tissue in order to provide electrical stimulation to the tongue, which is used to move the bolus to the pharynx in preparation for swallowing and to the muscles associated with the posterior neck region. As can be seen, the probe (which is preferably used as a common ground) is placed on the tongue and other electrodes are positioned bilaterally along the posterior neck region of the patient.

More specifically, as shown in FIG. 3C, a first electrode 18a and a second electrode 20a are connected to the probe, which is positioned in electrical contact with tissue to stimulate a motor point of the patient's tongue muscle. Most preferably, the probe includes a conductive ball that is positioned on the patient's tongue about the midpoint. Other electrodes 18b and 20b are positioned bilaterally in electrical contact with tissue to stimulate the patient's cervical paraspinal muscles. Most preferably, electrodes 18b and 20b each comprise a surface electrode that is positioned on the patient's skin in the posterior neck region just lateral to the one or more of the cervical vertebrae, most preferably near the C1, C2, C3 and/or C4 cervical vertebrae. The two channels thus use the probe as a common ground for application to the tongue. Of course, as an alternative to use of the probe, it should be understood that electrodes 18a and 18b could be placed side-by-side on the midpoint of the patient's tongue.

In this exemplary embodiment, the pulse train pattern comprises a biphasic overlapping pulse train pattern having the following parameters:

Pulse duration of individual electrical pulses: 50-70 microseconds

Current amplitude of individual electrical pulses: 15-50 milliamps

Duration of first phase: 100 milliseconds

Duration of overlap: 20 milliseconds

Duration of second phase: 100 milliseconds

Frequency of pulse train pattern: 0.6 seconds

Total treatment time: 20 minutes

Total number of treatments: 36

Frequency of individual electrical pulses (in each phase): 50 hertz

FOURTH EXEMPLARY EMBODIMENT

Figure 3D:
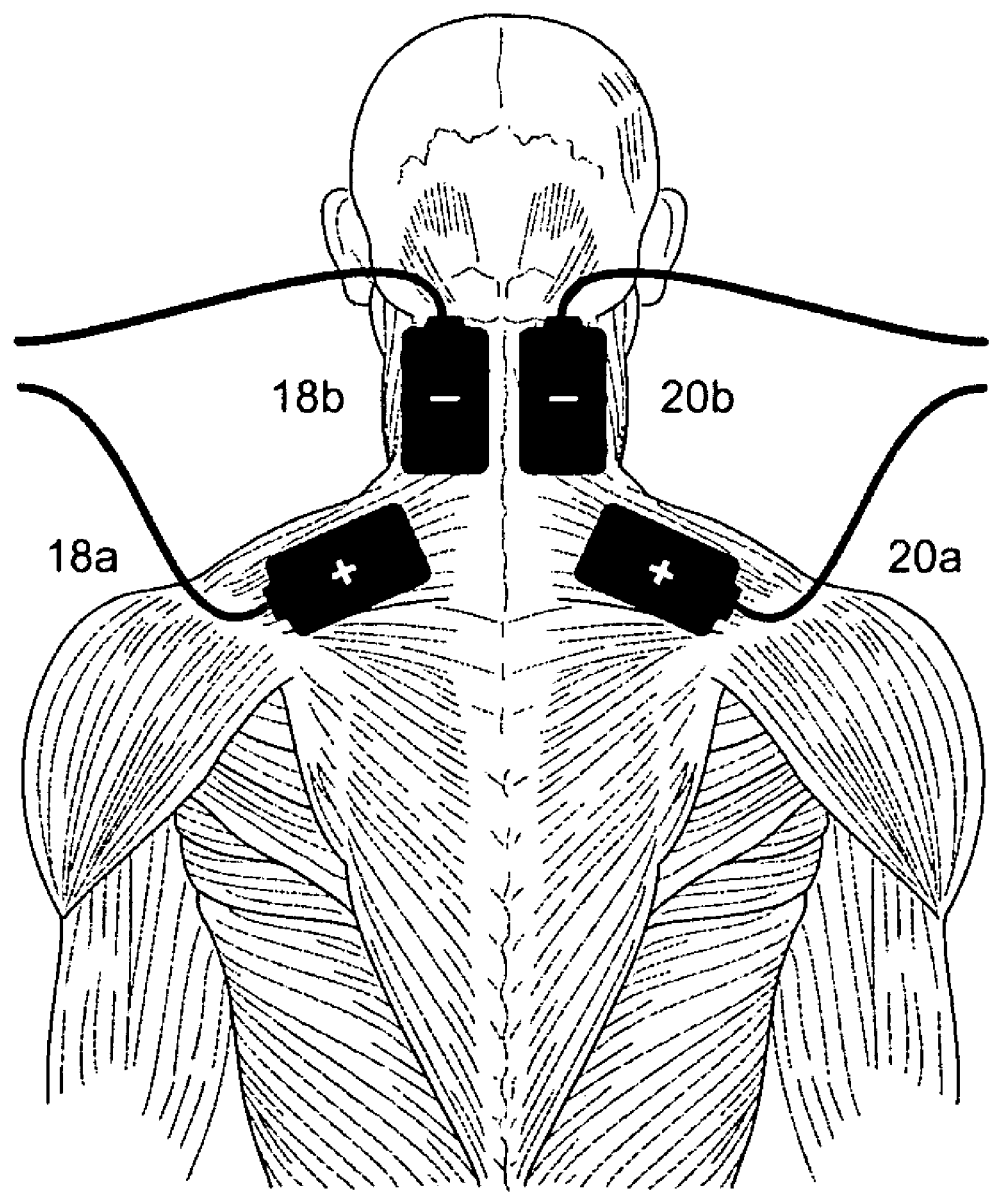
FIG. 3D illustrates a method for treating dysphagia in a patient by applying electrical stimulation in accordance with a fourth exemplary embodiment of the present invention, in which the trapezius muscles and the cervical paraspinal muscles of the patient are stimulated.

In a fourth exemplary embodiment of the present invention, as generally illustrated in FIG. 3D, a pair of electrodes is positioned in electrical contact with the patient's tissue in order to provide electrical stimulation to one or more of the muscles involved in the oropharyngeal phase of swallowing and to the muscles associated with the posterior neck region. A second pair of electrodes is positioned bilaterally in a similar manner.

More specifically, as shown in FIG. 3D, a first electrode 18a is positioned in electrical contact with tissue to stimulate a motor point of the patient's trapezius muscle. As discussed above, the spinal component of the accessory nerve (XI) innervates the trapezius muscle. The more superficial muscles, such as the trapezius, rhomboideus minor, and/or rhomboideus major associated with maintaining proper posture during swallowing, may also be stimulated. Most preferably, first electrode 18a comprises a surface electrode that is positioned on the patient's skin on the rhomboid and mid-trapezius, just lateral to the lower cervical and upper thoracic vertebrae, most preferably near the C7 cervical vertebrae and the T1 thoracic vertebrae. A second electrode 18b is positioned in electrical contact with tissue to stimulate the patient's cervical paraspinal muscles. Most preferably, second electrode 18b comprises a surface electrode that is positioned on the patient's skin in the posterior neck region just lateral to the one or more of the cervical vertebrae, most preferably near the C1, C2, C3 and/or C4 cervical vertebrae. Another pair of electrodes 20a, 20b is provided bilaterally in a similar position as generally illustrated in FIG. 3D.

In this exemplary embodiment, the pulse train pattern comprises a biphasic overlapping pulse train pattern having the following parameters:

Pulse duration of individual electrical pulses: 50-70 microseconds

Current amplitude of individual electrical pulses: 30-140 milliamps

Duration of first phase: 100 milliseconds

Duration of overlap: 20 milliseconds

Duration of second phase: 100 milliseconds

Frequency of pulse train pattern: 0.6 seconds

Total treatment time: 20 minutes

Total number of treatments: 36

Frequency of individual electrical pulses (in each phase): 50 hertz

FIFTH EXEMPLARY EMBODIMENT

Figure 3E:
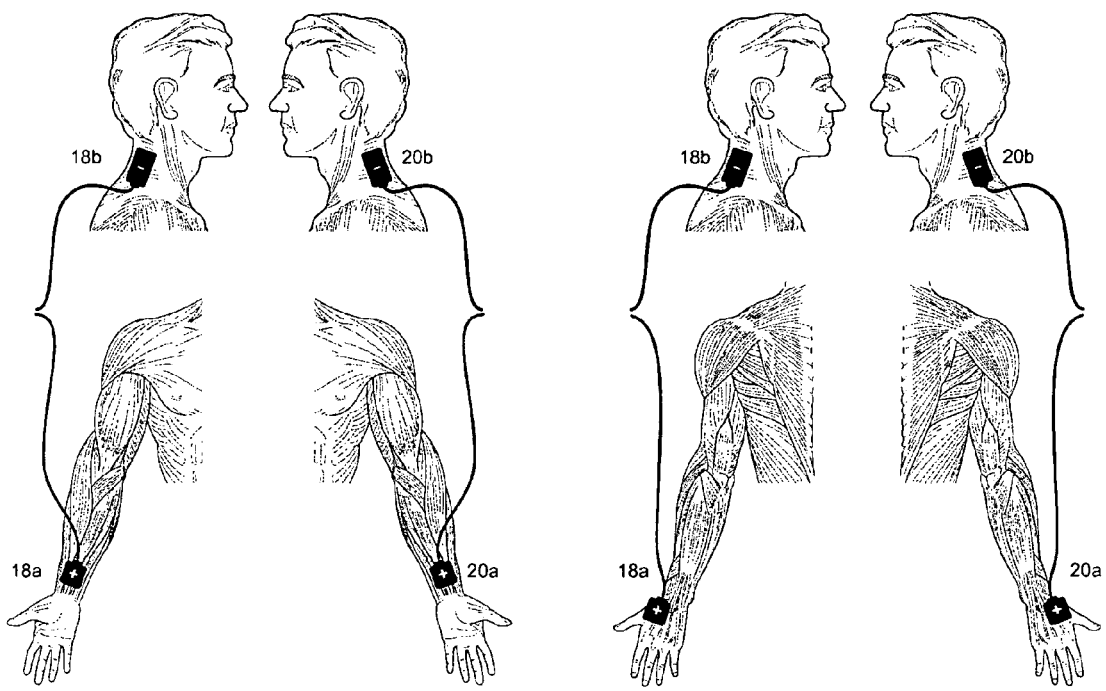
FIG. 3E illustrates a method for treating dysphagia in a patient by applying electrical stimulation in accordance with a fifth exemplary embodiment of the present invention, in which the median nerves or first dorsal interosseous muscles and the cervical paraspinal muscles of the patient are stimulated.

In a fifth exemplary embodiment of the present invention, as generally illustrated in FIG. 3E, a pair of electrodes is positioned in electrical contact with the patient's tissue in order to provide electrical stimulation to one or more of the muscles involved in the oropharyngeal and esophageal phase of swallowing and to muscles associated with the posterior neck region. A second pair of electrodes is positioned bilaterally in a similar manner.

More specifically, as shown in FIG. 3E, a first electrode 18a is positioned in electrical contact with tissue to stimulate the median nerve or first dorsal interosseous muscle. One or more muscles of the arm involved in carrying food to the patient's mouth may also be stimulated, such as the (superficial) flexor carpi radialis, flexor carpi ulnaris, palmaris longus brachioradialis, (deep) flexor digitorum superficalis, or flexor digitorum profundus. Most preferably, first electrode 18a comprises a surface electrode that is positioned on the patient's skin on the palmar/anterior side of the forearm at the base of the wrist just above the wrist crease. A second electrode 18b is positioned in electrical contact with tissue to stimulate the patient's cervical paraspinal muscles. Most preferably, the second electrode 18b comprises a surface electrode that is positioned on the patient's skin in the posterior neck region just lateral to the one or more of the cervical vertebrae, most preferably near the C1, C2, C3 and/or C4 cervical vertebrae. Another pair of electrodes 20a, 20b is provided bilaterally in a similar position as generally illustrated in FIG. 3E.

In this exemplary embodiment, the pulse train pattern comprises a triphasic overlapping pulse train pattern having the following parameters:
Pulse duration of individual electrical pulses: 50-70 microseconds
Current amplitude of individual electrical pulses: 30-70 milliamps
Duration of first phase: 100 milliseconds
Duration of overlap: 20 milliseconds
Duration of second phase: 100 milliseconds
Duration of overlap: 20 milliseconds
Duration of third phase: 60 milliseconds
Frequency of pulse train pattern: 0.5-1.5 seconds
Total treatment time: 20 minutes
Total number of treatments: 36
Frequency of individual electrical pulses (in each phase): 50 hertz

SIXTH EXEMPLARY EMBODIMENT

Figure 3F:
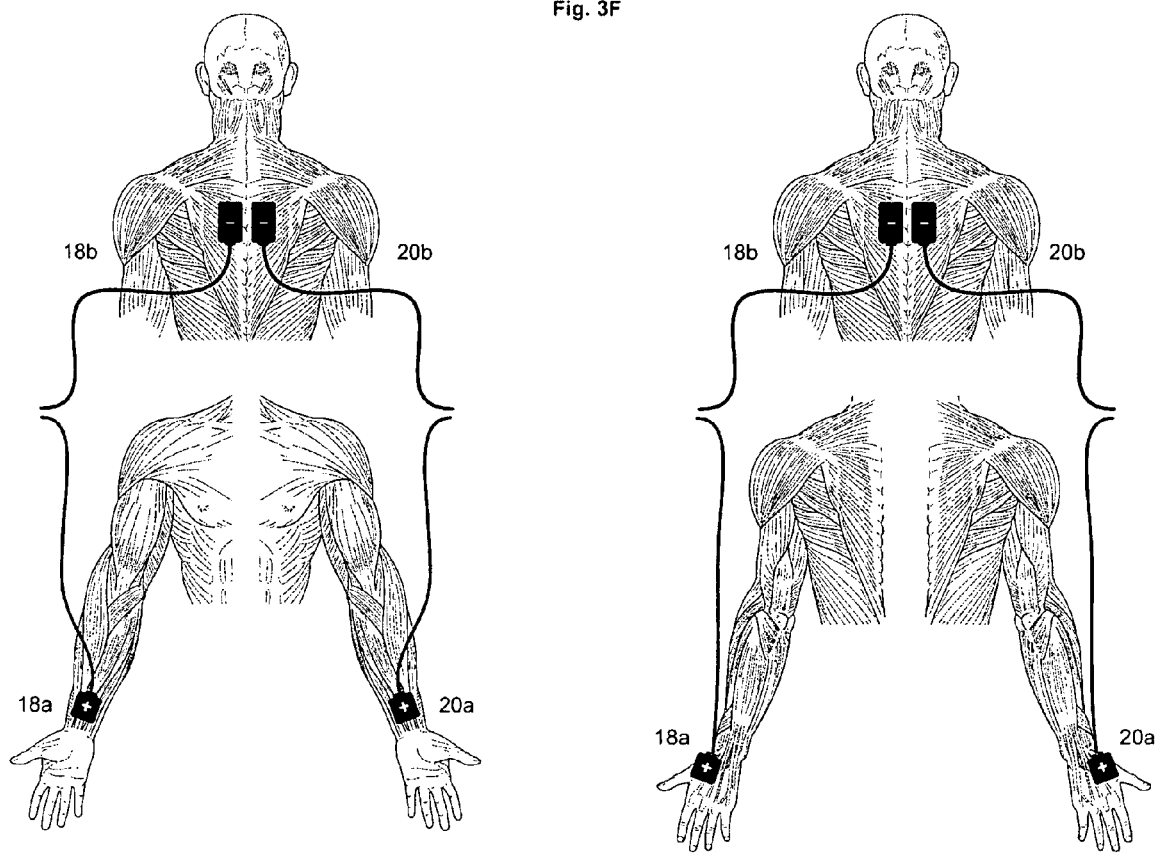
FIG. 3F illustrates a method for treating dysphagia in a patient by applying electrical stimulation in accordance with a sixth exemplary embodiment of the present invention, in which the median nerves or first dorsal interosseous muscles and the thoracic paraspinal muscles of the patient are stimulated.

In a sixth exemplary embodiment of the present invention, as generally illustrated in FIG. 3F, a pair of electrodes is positioned in electrical contact with the patient's tissue in order to provide electrical stimulation to one or more of the muscles involved in the oropharyngeal and esophageal phase of swallowing and to muscles associated with the posterior thoracic region. A second pair of electrodes is positioned bilaterally in a similar manner.

More specifically, as shown in FIG. 3F, a first electrode 18a is positioned in electrical contact with tissue to stimulate the median nerve or first dorsal interosseous muscle. One or more muscles of the arm involved in carrying food to the patient's mouth may also be stimulated, such as the (superficial) flexor carpi radialis, flexor carpi ulnaris, palmaris longus brachioradialis, (deep) flexor digitorum superficalis, or flexor digitorum profundus. Most preferably, first electrode 18a comprises a surface electrode that is positioned on the patient's skin on the palmar/anterior side of the forearm at the base of the wrist just above the wrist crease. A second electrode 18b is positioned in electrical contact with tissue to stimulate the patient's thoracic paraspinal muscles. Most preferably, the second electrode 18b comprises a surface electrode that is positioned on the patient's skin in the posterior thoracic region just lateral to the thoracic vertebrae, most preferably near the T4, T5, and/or T6 thoracic vertebrae. Another pair of electrodes 20a, 20b is provided bilaterally in a similar position as generally illustrated in FIG. 3F.

In this exemplary embodiment, the pulse train pattern comprises a triphasic overlapping pulse train pattern having the following parameters:
Pulse duration of individual electrical pulses: 50-70 microseconds
Current amplitude of individual electrical pulses: 30-70 milliamps
Duration of first phase: 100 milliseconds
Duration of overlap: 20 milliseconds
Duration of second phase: 100 milliseconds
Duration of overlap: 20 milliseconds
Duration of third phase: 60 milliseconds
Frequency of pulse train pattern: 0.5-1.5 seconds
Total treatment time: 20 minutes
Total number of treatments: 36
Frequency of individual electrical pulses (in each phase): 50 hertz

SEVENTH EXEMPLARY EMBODIMENT

Figure 3G:
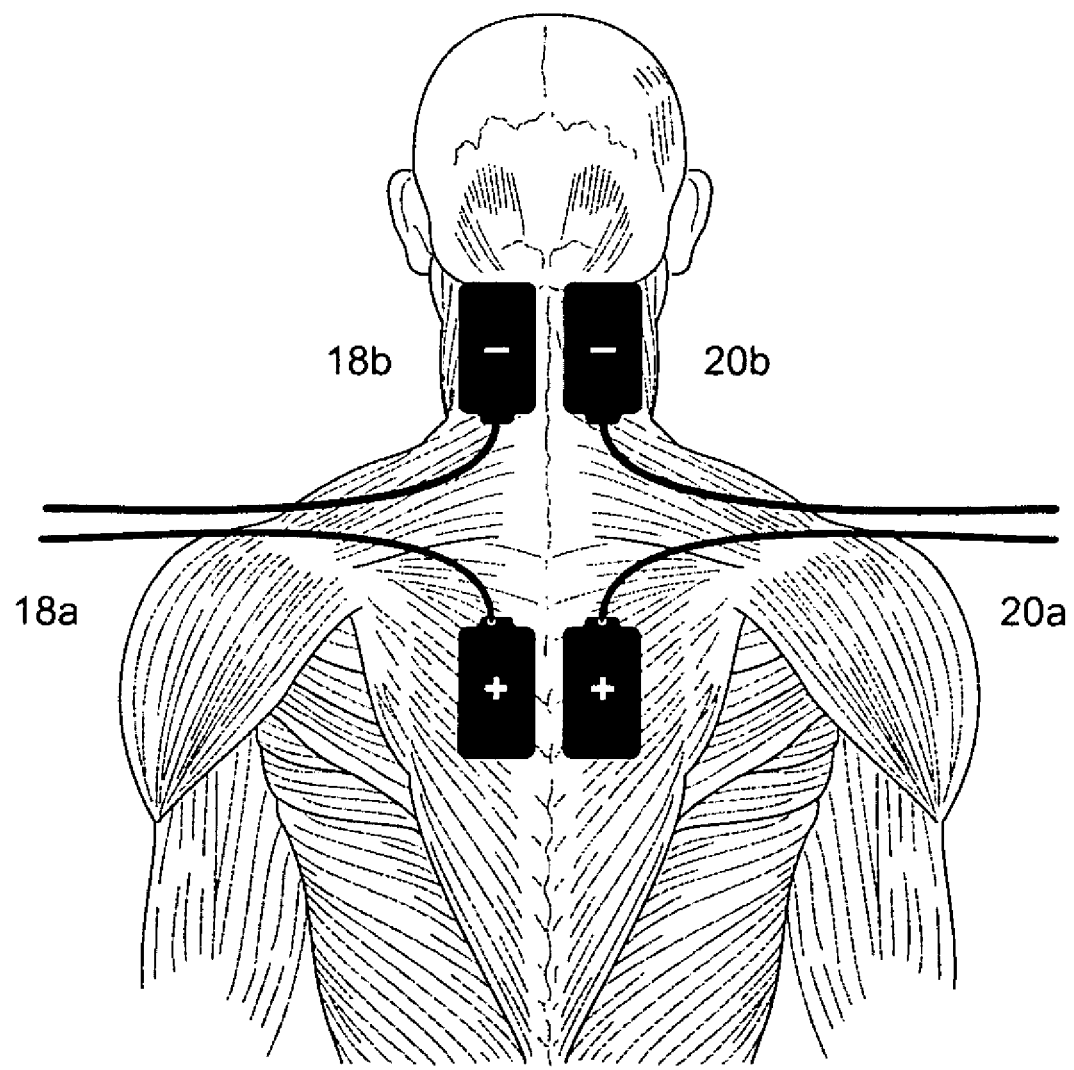
FIG. 3G illustrates a method for treating dysphagia in a patient by applying electrical stimulation in accordance with a seventh exemplary embodiment of the present invention, in which the thoracic paraspinal muscles and the cervical paraspinal muscles of the patient are stimulated.

In a seventh exemplary embodiment of the present invention, as generally illustrated in FIG. 3G, a pair of electrodes is positioned in electrical contact with the patient's tissue in order to provide electrical stimulation to one or more of the muscles in the posterior thoracic region involved in the esophageal phase of swallowing and to the muscles associated with the posterior neck region. A second pair of electrodes is positioned bilaterally in a similar manner.

More specifically, as shown in FIG. 3G, a first electrode 18a is positioned in electrical contact with tissue to stimulate the patient's thoracic paraspinal muscles at T4, T5, and/or T6 thoracic vertebrae. Most preferably, the first electrode 18a is positioned on the patient's skin in the posterior thoracic region, near the T4, T5, and/or T6 thoracic vertebrae. The second electrode 18b is positioned in electrical contact with tissue to stimulate the patient's cervical paraspinal muscles. Most preferably, second electrode 18b comprises a surface electrode that is positioned on the patient's skin in the posterior neck region just lateral to the one or more of the cervical vertebrae, most preferably near either (1) the C1, C2, C3 and/or C4 cervical vertebrae or (2) the C5, C6 and/or C7 cervical vertebrae. Another pair of electrodes 20a, 20b is provided bilaterally in a similar position as generally illustrated in FIG. 3G.

In this exemplary embodiment, the pulse train pattern comprises a biphasic overlapping pulse train pattern having the following parameters:
Pulse duration of individual electrical pulses: 50-70 microseconds
Current amplitude of individual electrical pulses: 30-140 milliamps
Duration of first phase: 100 milliseconds
Duration of overlap: 20 milliseconds
Duration of second phase: 100 milliseconds
Frequency of pulse train pattern: 0.6 seconds Total treatment time: 20 minutes Total number of treatments: 36

Frequency of individual electrical pulses (in each phase): 50 hertz

It will also be appreciated that the dysphagia treatment methods of the present invention may readily be adapted by configuring the electrodes in a manner that is asymmetrical or bilateral in nature, depending upon the stage of dysphagia being treated. For example, for patients suffering from oropharyngeal and esophageal dysphagia at the same time, a combination of the Fifth and Seventh exemplary embodiments may be used. That is, for the first channel, the first electrode 18a may be positioned to stimulate the median nerve or first dorsal interosseus muscle of the patient by placing the electrode 18a on the palmar/anterior side of the forearm at the base of the wrist. The second electrode 18b of the first channel positioned to stimulate the patient's cervical paraspinal muscles in the said posterior neck region near the C1, C2, C3, and/or C4 cervical vertebrae. For the second channel, the first electrode 20a may be positioned so as stimulate the thoracic paraspinal muscles in the posterior thoracic region (e.g. near the T4, T5, and/or T6 thoracic vertebrae of said patient). The second electrode 20b of the second channel is positioned to stimulate the posterior neck region near the C1, C2, C3, and/or C4 cervical vertebrae of said patient. It is contemplated that all of the Exemplary embodiments may be combined in a similar manner to fit the patient's needs and symptoms (e.g. first embodiment for the first channel and either the second, third, fourth, fifth, sixth, or seventh embodiments for the second channel, and so on). In each embodiment, however, it is contemplated that at least one of the electrodes in each channel will be positioned in electrical contact with the patient's posterior neck region or posterior thoracic region.

Case Study #1

This case study involved a 57-year-old female suffering from chronic esophageal dysmotility over the past four years. The patient's medical history includes two strokes involving right fronto-parietal lobe infarction about five years ago and left temporal parietal infarction about four years ago. The patient exhibited excellent upper and lower extremity recovery with some residual left hand weakness. The patient also suffered from chronic gastroesophageal reflux disease ("GERD"), requiring antacids for past four years. While ingestion of liquids and puree solids had not been a significant problem, the patient had been unable to tolerate chicken and even ground meat without extensive time between swallows. The patient showed evidence of esophageal regurgitation on modified barium swallow. In addition, recent respiratory failure required intubation and ventilation about four weeks prior to treatment as discussed herein.

The patient was treated with Omnistim® $FX^2$ electrical stimulation using therapy combination discussed with respect to the Fifth and Seventh Exemplary Embodiments. More specifically, for Channel A, the positive electrode (2"×4") was applied to the right hand first dorsal interosseous muscle and the negative electrode was applied to the right C1-C4 paraspinal muscles. For Channel B, the positive electrode was applied to the left intrascapular paraspinal/mid thoracic muscles (T4-T6) and the negative electrode was applied to the left C1-C4 paraspinal muscles.

The intensity was such to create minimal twitch muscle contractions. The pulse train pattern comprises a biphasic overlapping pulse train pattern having the following parameters:

Pulse duration of individual electrical pulses: 50 microseconds

Current amplitude of individual electrical pulses: 60-70 milliamps

Duration of first phase: 100 milliseconds (5 pulses per train)

Duration of overlap: 20 milliseconds (1 pulse)

Duration of second phase: 100 milliseconds (5 pulses per train)

Frequency of pulse train pattern: 0.6 seconds (1.6 Hz)

Total treatment time: 20 minutes

Frequency of individual electrical pulses (in each phase): 50 hertz

After stimulation, the patient had no difficulty swallowing "rather dry" chicken. Further, regurgitation during and after full meal was no longer noted. The effect of treatment noted to be greater than 6 hours initially and extended with repeated daily treatments. No pain was noted during or after treatment.

Case Study #2

This case study involved a 63-year-old male with advanced Parkinson's Disease and severe rigidity affecting both oral and pharyngeal phase of swallowing. The patient was unable to open his mouth sufficiently to take his dopaminergic medication. Further, the patient could not tolerate a nasogastric tube.

The patient was treated with Omnistim® $FX^2$ electrical stimulation with a therapy protocol generally discussed with respect to the Fourth Exemplary Embodiment. More specifically, for Channel A, the positive electrode (2"×4") was applied to the right upper trapezius muscle and the negative electrode was applied to the right C1-C4 paraspinal muscles. For Channel B, the positive electrode (2"×4") was applied to the left upper trapezius muscle, and the negative electrode was applied to the left C1-C4 paraspinal muscles.

The intensity was such to create minimal twitch muscle contractions with visible contractions and minimal head movement. The pulse train pattern comprises a biphasic overlapping pulse train pattern having the following parameters:

Pulse duration of individual electrical pulses: 50 microseconds

Current amplitude of individual electrical pulses: 60-80 milliamps

Duration of first phase: 100 milliseconds (5 pulses per train)

Duration of overlap: 20 milliseconds (1 pulse)

Duration of second phase: 100 milliseconds (5 pulses per train)

Frequency of pulse train pattern: 0.6 seconds (1.6 Hz)

Total treatment time: 20 minutes

Frequency of individual electrical pulses (in each phase): 50 hertz

During the final five minutes and following the treatment, the patient was able to voluntarily move his head approximately 20 degrees in each direction. The patient had not been able to do this prior to the stimulation. The patient as then able to open his mouth voluntarily in order to ingest medication with applesauce. The initial benefit lasted approximately four hours. Repeated daily applications provided progressive improvement to the point that the patient was able to resume feeding with mechanically softened foods and ingest medications without aspiration. After four sessions, the benefit lasted over 12 hours at each application. At discharge from the hospital, the patient used the system described above three times per week with continued benefit for three months. Oral and esophageal phases of swallowing continued to be intact during that time.

Case Study #3

This case study involved an 82-year-old male with oral and pharyngeal phase dysphagia due to left cerebellar hemorrhage. Aspiration was noted on modified barium swallow. Tongue and pharyngeal dysmotility was noted, including a reduction in the initiation of the swallowing reflex. Gastrostomy tube placement had been required. The patient was readmitted with marked weakness due to aspiration pneumonia and urinary tract infection exacerbating prior left hemiparesis and ataxia. The patient also reported a pain in the tongue due to candida overgrowth.

The patient was treated with Omnistim® FX$^2$ electrical stimulation with a therapy protocol generally set forth in the First Exemplary Embodiment. More specifically, for Channel A, the positive electrode (2"×2") was applied to the right facial musculature (orbicularis oris and buccinator) and the negative electrode was applied to the right C1-C4 paraspinal muscles. For Channel B, the positive electrode (2"×2") was applied to the left facial musculature (orbicularis oris and buccinators) and the negative electrode was applied to the left C1-C4 paraspinal muscles.

The intensity was such to create minimal twitch muscle contractions with visible contractions and minimal head movement. The pulse train pattern comprises a biphasic overlapping pulse train pattern having the following parameters:

Pulse duration of individual electrical pulses: 50 microseconds

Current amplitude of individual electrical pulses: 45-65 milliamps

Duration of first phase: 100 milliseconds (5 pulses per train)

Duration of overlap: 20 milliseconds (1 pulse)

Duration of second phase: 100 milliseconds (5 pulses per train)

Frequency of pulse train pattern: 0.6 seconds (1.6 Hz)

Total treatment time: 20 minutes

Frequency of individual electrical pulses (in each phase): 50 hertz

The patient was able to tolerate progressive increase in intensity to create motor movement both the facial muscles as well as a minimal twitch of the cervical paraspinals. Following the first session, the patient was able to move his facial muscles and tongue better, but was unable to initiate a swallow nor was he able to manipulate ice chips. The patient's speech volume and precision was improved, the patient reported no discomfort from the treatment.

Following the second treatment the following day, the patient was able to manipulate the ice chips but could not tolerate the intensity of cold at mid-tongue. Softened ice cream was tolerated and he was able to both manipulate the small bolus and swallow. This generated a cough reflex as well as a double swallowing reflex.

Following the third treatment the following day, patient was able to speak more clearly, clear his throat more easily and generate a swallowing reflex both with a small bolus of ice cream as well as small sips of thickened water. Protective cough reflex was also reestablished.

Case Study #4

This case study involved a 76-year-old female with right middle cerebral artery ("MCA") ischemic infarction, left hemiparesis and dysphagia. Modified barium swallow after nasogastric tube removed demonstrated decreased oral phase motility and difficulty with initiation of swallowing reflex plus some penetration without aspiration with thickened consistency food.

The patient was treated with Omnistim® FX$^2$ electrical stimulation as generally set forth with respect to the First Exemplary Embodiment. More specifically, for Channel A, the positive electrode (2"×2") was applied to the right facial musculature (orbicularis oris and buccinator) and the negative electrode was applied to the right C1-C4 paraspinal muscles. For Channel B, the positive electrode (2"×2") was applied to the left facial musculature (orbicularis oris and buccinators) and the negative electrode was applied to the left C1-C4 paraspinal muscles.

The intensity was such to create minimal twitch muscle contractions with visible contractions and minimal head movement. The pulse train pattern comprises a biphasic overlapping pulse train pattern having the following parameters:

Pulse duration of individual electrical pulses: 50 microseconds

Current amplitude of individual electrical pulses: 40-60 milliamps

Duration of first phase: 100 milliseconds (5 pulses per train)

Duration of overlap: 20 milliseconds (1 pulse)

Duration of second phase: 100 milliseconds (5 pulses per train)

Frequency of pulse train pattern: 0.6 seconds (1.6 Hz)

Total treatment time: 20 minutes

Frequency of individual electrical pulses (in each phase): 50 hertz

The stimulation was well tolerated and patient stated that her face felt "more like my own." The patient also demonstrated an improvement in oral motility and pharyngeal phase of swallowing after the first session. She also had a complete reduction in choking after three sessions. Left hemiparesis partially improved after three weeks of inpatient rehabilitation but she no longer noted clinical dysphagia.

Case Study #5

This case study involved a 76-year-old male with idiopathic dysphagia who demonstrated a progressive decreased ability to activate the swallowing reflex. The patient has suffered increased choking over a three week period, an was referred for a placement of a gastrostomy tube. The patient reported that thin and thickened liquids were difficult to swallow. However, no oral phase dysfunction and no esophageal dysmotility was apparent. The patient had lost considerable weight (about 20 pounds) at the time of initiation of stimulation treatment.

The patient was treated with Grass S-88 electrical stimulator as generally set forth with respect to the Fourth Exemplary Embodiment. More specifically, for Channel A, the positive electrode (2"×4") was applied to the right upper trapezius muscle and the negative electrode applied to the right C1-C4 paraspinal muscles. For Channel B, the positive electrode (2"×4") was applied to the left upper trapezius muscle, and the negative electrode was applied to the left C1-C4 paraspinal muscles.

The intensity was such to create minimal twitch muscle contractions with visible contractions and minimal head movement. The pulse train pattern comprises a biphasic overlapping pulse train pattern having the following parameters:

Pulse duration of individual electrical pulses: 50 microseconds

Current amplitude of individual electrical pulses: 60-80 milliamps

Duration of first phase: 100 milliseconds (5 pulses per train)

Duration of overlap: 20 milliseconds (1 pulse)

Duration of second phase: 100 milliseconds (5 pulses per train)

Frequency of pulse train pattern: 0.6 seconds (1.6 Hz)

Total treatment time: 20 minutes

Frequency of individual electrical pulses (in each phase): 50 hertz

The patient reported that the treatment was well tolerated, and no pain was identified. Immediately after the first session, the patient was able to swallow tap water without difficulty and without choking. The benefit was reported to last about six hours, and subsequent treatments at a frequency of three times per week over the next three weeks eliminated the dysfunction. The patient had a relapse at about two months and resumed therapy which was immediately responsive requiring only three additional treatments.

At follow-up in three months, the patient continued to do well without requiring additional treatments. At four months post-treatment, however, the patient again had a relapse and continued on intermittent treatment using the Omnistim® $FX^2$ without a definitive diagnosis.

Case Study #6

This case study involved an 82-year-old male with Parkinson's plus syndrome causing dysphagia and difficulty with the oral phase of swallowing and chewing. The patient pocketed food in the bilateral cheeks and had difficulty with power of chewing. Also, the patient had difficulty with initiating the swallowing reflex.

The patient was treated with Omnistim® $FX^2$ electrical stimulation as generally set forth with respect to the Second Exemplary Embodiment. More specifically, for Channel A, the positive electrode (2"×2") was applied to the right facial musculature (masseter) and the negative electrode applied to the right C1-C4 paraspinal muscles. For Channel B, the positive electrode (2"×2") was applied to the left facial musculature (masseter) and the negative electrode was applied to the left C1-C4 paraspinal muscles.

The intensity was such to create minimal twitch muscle contractions with visible contractions and minimal head movement. The pulse train pattern comprises a biphasic overlapping pulse train pattern having the following parameters:

Pulse duration of individual electrical pulses: 50 microseconds

Current amplitude of individual electrical pulses: 35-58 milliamps

Duration of first phase: 100 milliseconds (5 pulses per train)

Duration of overlap: 20 milliseconds (1 pulse)

Duration of second phase: 100 milliseconds (5 pulses per train)

Frequency of pulse train pattern: 0.6 seconds (1.6 Hz)

Total treatment time: 20 minutes

Frequency of individual electrical pulses (in each phase): 50 hertz

The patient tolerated three sessions without difficulty. Effects were quite positive in that he was able to chew and swallow with more power and ease of mouth and tongue mobility. The effects lasted for 12 to 48 hrs following the treatments.

While the present invention has been described and illustrated hereinabove with reference to several exemplary embodiments, it should be understood that various modifications could be made to these embodiments without departing from the scope of the invention. Therefore, the invention is not to be limited to the exemplary embodiments described and illustrated hereinabove, except insofar as such limitations are included in the following claims.

What is claimed and desired to be secured by Letters Patent is as follows:

1. A method for treating dysphagia in a patient by electrical stimulation, said method comprising:

positioning a first channel comprising two electrodes, wherein a first electrode of said first channel is positioned in electrical contact with tissue of a first target region of said patient and a second electrode of said first channel is positioned in electrical contact with tissue of a posterior neck region or a posterior thoracic region of said patient using transcutaneous or percutaneous electrodes on said tissue of said posterior neck region or said posterior thoracic region;

positioning a second channel comprising two electrodes, wherein a first electrode of said second channel is positioned in electrical contact with tissue of a second target region of said patient and a second electrode of said second channel is positioned in electrical contact with tissue of said posterior neck region or said posterior thoracic region of said patient using transcutaneous or percutaneous electrodes on said tissue of said posterior neck region or said posterior thoracic region;

applying a series of electrical pulses to said patient through said first and second channels in accordance with a procedure for treating dysphagia.

2. The method of claim 1, wherein said first electrode of said first channel is positioned so as to stimulate a motor point of a first buccinator muscle of said patient and said first electrode of said second channel is positioned bilaterally so as to stimulate a motor point of a second buccinator muscle of said patient.

3. The method of claim 2, wherein said second electrode of said first channel and said second electrode of said second channel are positioned bilaterally so as to stimulate the cervical paraspinal muscles in said posterior neck region near the C1, C2, C3, and/or C4 cervical vertebrae of said patient.

4. The method of claim 1, wherein said first electrode of said first channel is positioned so as to stimulate a motor point of a first masseter muscle of said patient and said first electrode of said second channel is positioned bilaterally so as to stimulate a motor point of a second masseter muscle of said patient.

5. The method of claim 4, wherein said second electrode of said first channel and said second electrode of said second channel are positioned bilaterally so as to stimulate the cervical paraspinal muscles in said posterior neck region near the C1, C2, C3, and/or C4 cervical vertebrae of said patient.

6. The method of claim 1, wherein said first electrode of said first channel and said first electrode of said second channel are positioned so as to stimulate a tongue muscle of said patient.

7. The method of claim 6, wherein said second electrode of said first channel and said second electrode of said second channel are positioned bilaterally so as to stimulate the cervical paraspinal muscles in said posterior neck region near the C1, C2, C3, and/or C4 cervical vertebrae of said patient.

8. The method of claim 1, wherein said first electrode of said first channel is positioned so as to stimulate a motor point of a first trapezius muscle of said patient and said first electrode of said second channel is positioned bilaterally so as to stimulate a motor point of a second trapezius muscle of said patient.

9. The method of claim 8, wherein said second electrode of said first channel and said second electrode of said second channel are positioned bilaterally so as to stimulate the cervical paraspinal muscles in said posterior neck region near the C1, C2, C3, and/or C4 cervical vertebrae of said patient.

10. The method of claim 1, wherein said first electrode of said first channel is positioned so as to stimulate a first median nerve of said patient and said first electrode of said second channel is positioned bilaterally so as to stimulate a second median nerve of said patient.

11. The method of claim 10, wherein said second electrode of said first channel and said second electrode of said second channel are positioned bilaterally so as to stimulate the cervical paraspinal muscles in said posterior neck region near the C1, C2, C3, and/or C4 cervical vertebrae of said patient.

12. The method of claim 10, wherein said second electrode of said first channel and said second electrode of said second channel are positioned bilaterally so as to stimulate the cervical paraspinal muscles in said posterior neck region near the C4, C5, C6, and/or C7 cervical vertebrae of said patient.

13. The method of claim 10, wherein said second electrode of said first channel and said second electrode of said second channel are positioned bilaterally so as to stimulate the thoracic paraspinal muscles in said posterior thoracic region near the T4, T5, and/or T6 thoracic vertebrae of said patient.

14. The method of claim 1, wherein said first electrode of said first channel is positioned so as to stimulate a motor point of a firstly located first dorsal interosseous muscle of said patient and said first electrode of said second channel is positioned bilaterally so as to stimulate a motor point of a secondly located first dorsal interosseous muscle of said patient.

15. The method of claim 14, wherein said second electrode of said first channel and said second electrode of said second channel are positioned bilaterally so as to stimulate the cervical paraspinal muscles in said posterior neck region near the C1, C2, C3, and/or C4 cervical vertebrae of said patient.

16. The method of claim 14, wherein said second electrode of said first channel and said second electrode of said second channel are positioned bilaterally so as to stimulate the cervical paraspinal muscles in said posterior neck region near the C4, C5, C6, and/or C7 cervical vertebrae of said patient.

17. The method of claim 14, wherein said second electrode of said first channel and said second electrode of said second channel are positioned bilaterally so as to stimulate the thoracic paraspinal muscles in said posterior thoracic region near the T4, T5, and/or T6 thoracic vertebrae of said patient.

18. The method of claim 1, wherein said first electrode of said first channel and said first electrode of said second channel are positioned bilaterally so as to stimulate the thoracic paraspinal muscles in said posterior thoracic region near the T4, T5, and/or T6 thoracic vertebrae of said patient.

19. The method of claim 18, wherein said second electrode of said first channel and said second electrode of said second channel are positioned bilaterally so as to stimulate the cervical paraspinal muscles in said posterior neck region near the C1, C2, C3, and/or C4 cervical vertebrae of said patient.

20. The method of claim 18, wherein said second electrode of said first channel and said second electrode of said second channel are positioned bilaterally so as to stimulate the cervical paraspinal muscles in said posterior neck region near the C5, C6, and/or C7 cervical vertebrae of said patient.

21. The method of claim 1, wherein said first electrode of said first channel is positioned to stimulate a motor point of a firstly located first dorsal interosseous muscle of said patient and said second electrode of said first channel is positioned so as to stimulate said posterior neck region near the C1, C2, C3, and/or C4 cervical vertebrae of said patient, and said first electrode of said second channel is positioned so as stimulate the thoracic paraspinal muscles in said posterior thoracic region near the T4, T5, and/or T6 thoracic vertebrae of said patient and said second electrode of said second channel is positioned so as to stimulate the posterior neck region near the C1, C2, C3, and/or C4 cervical vertebrae of said patient.

22. The method of claim 1, wherein said series of electrical pulses comprises a plurality of cycles of a biphasic sequential pulse train pattern.

23. The method of claim 22, wherein said biphasic sequential pulse train pattern comprises a first phase of electrical pulses applied to said first channel and a second phase of electrical pulses applied to said second channel, wherein said second phase of electrical pulses commences after termination of said first phase of electrical pulses.

24. The method of claim 1, wherein said series of electrical pulses comprises a plurality of cycles of a biphasic overlapping pulse train pattern.

25. The method of claim 21 wherein said biphasic overlapping pulse train pattern comprises a first phase of electrical pulses applied to said first channel and a second phase of electrical pulses applied to said second channel, wherein said second phase of electrical pulses commences before termination of said first phase of electrical pulses.

26. The method of claim 1, wherein said series of electrical pulses comprises a plurality of cycles of a triphasic sequential pulse train pattern.

27. The method of claim 26, wherein said triphasic sequential pulse train pattern comprises a first phase of electrical pulses applied to said first channel, a second phase of electrical pulses applied to said second channel, and a third phase of electrical pulses applied to said first channel, wherein said second phase of electrical pulses commences after termination of said first phase of electrical pulses and wherein said third phase of electrical pulses commences after termination of said second phase of electrical pulses.

28. The method of claim 1, wherein said series of electrical pulses comprises a plurality of cycles of a triphasic overlapping pulse train pattern.

29. The method of claim 28, wherein said triphasic overlapping pulse train pattern comprises a first phase of electrical pulses applied to said first channel, a second phase of electrical pulses applied to said second channel, and a third phase of electrical pulses applied to said first channel, wherein said second phase of electrical pulses commences before termination of said first phase of electrical pulses and wherein said third phase of electrical pulses commences before termination of said second phase of electrical pulses.

30. The method of claim 1, wherein said series of electrical pulses comprises a functional pulse train pattern applied to said first and second channels so as to mimic electrical sequencing of particular muscles involved in swallowing during normal functioning activity.

31. The method of claim 1, wherein each of said electrical pulses has a pulse duration of between 30 microseconds and 100 microseconds.

32. The method of claim 1, wherein each of said electrical pulses has a current amplitude of between 25 milliamps and 140 milliamps.

33. A method for treating dysphagia in a patient by electrical stimulation, said method comprising:
positioning at least one channel comprising two electrodes, wherein a first electrode is positioned in electrical contact with tissue of a target region of said patient and a second electrode is positioned in electrical contact with tissue of a posterior neck region or a posterior thoracic region of said patient using transcutaneous or percutaneous electrodes on said tissue of said posterior neck region or said posterior thoracic region; and
applying a series of electrical pulses to said patient through said channel in accordance with a procedure for treating dysphagia.

34. The method of claim 33, wherein said first electrode is positioned so as to stimulate a motor point of a buccinator muscle of said patient.

35. The method of claim 33, wherein said first electrode is positioned so as to stimulate a motor point of a masseter muscle of said patient.

36. The method of claim 33, wherein said first electrode is positioned so as to stimulate a tongue muscle of said patient.

37. The method of claim 33, wherein said first electrode is positioned so as to stimulate a motor point of a trapezius muscle of said patient.

38. The method of claim 33, wherein said first electrode is positioned so as to stimulate a median nerve of said patient.

39. The method of claim 33, wherein said first electrode is positioned so as to stimulate a motor point of a first dorsal interosseous muscle of said patient.

40. The method of claim 33, wherein said first electrode is positioned so as to stimulate a thoracic paraspinal muscle of said patient.

41. The method of claim 33, wherein said second electrode is positioned so as to stimulate the cervical paraspinal muscles in said posterior neck region near the C1, C2, C3 and/or C4 cervical vertebrae of said patient.

42. The method of claim 33, wherein said second electrode is positioned so as to stimulate the cervical paraspinal muscles in said posterior neck region near the C5, C6, and/or C7 cervical vertebrae of said patient.

43. The method of claim 33, wherein said second electrode is positioned so as to stimulate the thoracic paraspinal muscles in said posterior thoracic region near the T4, T5, and/or T6 thoracic vertebrae of said patient.

44. The method of claim 33, wherein said series of electrical pulses comprises a low-frequency pulse train pattern.

45. The method of claim 44, wherein said low-frequency pulse train pattern comprises individual electrical pulses generated at a frequency of between 0.1 Hz and 200 Hz.

46. The method of claim 33, wherein said series of electrical pulses comprises a frequency-sequenced pulse burst train pattern with a carrier frequency of between 500 Hz and 100,000 Hz.

47. The method of claim 46, wherein said frequency-sequenced pulse burst train pattern comprises a first sequence of modulated electrical pulses generated at a burst frequency of between 0.1 Hz and 5 Hz, a second sequence of modulated electrical pulses generated at a burst frequency of between 5 Hz and 20 Hz, and a third sequence of modulated electrical pulses generated at a burst frequency of between 20 Hz and 250 Hz.

48. The method of claim 46, wherein said frequency-sequenced pulse burst train pattern comprises a first sequence of modulated electrical pulses generated at a burst frequency of between 5 Hz and 20 Hz, a second sequence of modulated electrical pulses generated at a burst frequency of between 0.1 Hz and 5 Hz, and a third sequence of modulated electrical pulses generated at a burst frequency of between 20 Hz and 250 Hz.

49. The method of claim 46, wherein said frequency-sequenced pulse burst train pattern comprises a first sequence of modulated electrical pulses generated at a burst frequency of between 20 Hz and 250 Hz, and a second sequence of modulated electrical pulses generated at a burst frequency of between 0.1 Hz and 5 Hz.

50. The method of claim 33, wherein each of said electrical pulses has a pulse duration of between 30 microseconds and 100 microseconds.

51. The method of claim 33, wherein each of said electrical pulses has a current amplitude of between 25 milliamps and 140 milliamps.

* * * * *